(12) United States Patent
Kogasaka et al.

(10) Patent No.: US 7,491,165 B2
(45) Date of Patent: Feb. 17, 2009

(54) SURGICAL SYSTEM

(75) Inventors: Takahiro Kogasaka, Hachioji (JP); Masayuki Irie, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/872,992

(22) Filed: Jun. 21, 2004

(65) Prior Publication Data
US 2005/0004431 A1    Jan. 6, 2005

(30) Foreign Application Priority Data
Jun. 23, 2003    (JP) .............................. 2003-178341

(51) Int. Cl.
*A61B 1/00* (2006.01)
(52) U.S. Cl. .................. 600/104; 600/103; 600/108; 600/113; 600/114; 600/117; 600/118; 600/153; 606/1
(58) Field of Classification Search ................ 600/103, 600/108, 113–114, 117–118
See application file for complete search history.

(56) References Cited

U.S. PATENT DOCUMENTS

| 4,830,460 A | 5/1989 | Goldenberg | |
| 5,368,015 A | 11/1994 | Wilk | |
| 5,572,999 A | 11/1996 | Funda et al. | |
| 5,916,150 A * | 6/1999 | Sillman | 600/184 |
| 6,036,637 A * | 3/2000 | Kudo | 600/173 |
| 6,352,503 B1* | 3/2002 | Matsui et al. | 600/104 |
| 6,475,138 B1* | 11/2002 | Schechter et al. | 600/108 |
| 2002/0147384 A1* | 10/2002 | Uchikubo | 600/109 |
| 2003/0013949 A1 | 1/2003 | Moll et al. | |

FOREIGN PATENT DOCUMENTS

| EP | 1 250 891 A2 | 10/2002 |
| JP | 5-337073 | 12/1993 |
| WO | WO 03/017859 A1 | 3/2003 |

* cited by examiner

*Primary Examiner*—Linda C Dvorak
*Assistant Examiner*—Matthew J Kasztejna
(74) *Attorney, Agent, or Firm*—Scully, Scott, Murphy & Presser, P.C.

(57) ABSTRACT

A surgical system according to the present invention comprises: a surgical instrument for medical treatment of an affected portion in the body cavity; an observation device for observing tissue in the body cavity; an image display device for displaying images taken by the observation device; and an indicating-point control device included in at least one of the surgical instrument and the observation device, for controlling the position of an indicating point superimposed on an image displayed on the image display device.

16 Claims, 24 Drawing Sheets

SURGICAL SYSTEM

This application claims benefit of Japanese Application No. 2003-178341 filed on Jun. 23, 2003, the contents of which are incorporated by this reference.

BACKGROUND OF THE INVENTION

1. Field of the Invention

The present invention relates to a surgical system wherein the surgeon performs surgical treatment in cooperation with multiple surgical staff members such as assistants to the surgeon, nurses, and the like, while observing images of tissue in the body cavity taken by an endoscope.

2. Description of the Related Art

In general, surgical treatment is widely performed using an endoscope. In this kind of surgical treatment, the surgeon makes multiple openings in the body wall of the patient, wherein one is used for inserting an endoscope, and the others are used for inserting surgical instruments. Subsequently, the surgeon performs medical treatment of tissue in the body cavity with the surgical instruments while observing images of the tissue in the body cavity taken by the endoscope. In general, such a surgical treatment is performed by the surgeon who operates the surgical instruments and the endoscope, in cooperation with surgical assistants, nurses, and the like, who assist the surgeon around the surgery table. The surgical assistants, nurses, and the like, operate surgical instruments other than the endoscope, or in some case, operate the endoscope, instead of the surgeon. The surgical staff members perform surgery while communicating with each other.

On the other hand, a medical instrument is disclosed in Japanese Unexamined Patent Application Publication No. 5-337073, wherein a surgical instrument or a guide tube of the surgical instrument includes guide means for guiding such that the tip of the surgical instrument comes in the field of view of the endoscope. Thus, the surgeon can grasp the direction of the surgical instrument even in the event that the surgical instrument is out of the field of view of the endoscope during surgery.

SUMMARY OF THE INVENTION

A surgical system according to the present invention comprises: a surgical instrument for medical treatment of an affected portion in the body cavity; an observation device for observing tissue in the body cavity; an image display device for displaying images taken by the observation device; and an indicating-point control device included in at least one of the surgical instrument and the observation device, for controlling the position of an indicating point superimposed on an image displayed on the image display device.

BRIEF DESCRIPTION OF THE DRAWINGS

FIG. 4 is a longitudinal cross-sectional diagram which shows a configuration of a laser forceps holder;

FIG. 5 is a partial cross-sectional diagram which shows a laser forceps holder with forceps mounted thereon;

FIG. 6 is a diagram for describing indicating-point superimposing means according to a third embodiment of the present invention;

FIG. 7 is a partial cross-sectional diagram which shows a joy-stick unit according to the third embodiment of the present invention;

FIG. 11 is a diagram for describing surgery using an endoscopic surgical system according to the seventh embodiment;

FIG. 12 is a schematic diagram which shows a configuration of a first surgical instrument according to the seventh embodiment;

FIG. 13 is a diagram for describing actions of a holder for an surgical instrument of the surgical system according to the seventh embodiment;

FIG. 14 is a front view which shows the tip of a sheath of the surgical instrument of the surgical system according to the seventh embodiment;

FIG. 15 is a cross-sectional view taken along line XV-XV in FIG. 14;

FIG. 16 is a cross-sectional view taken along line XVI-XVI in FIG. 14;

FIG. 17 is a plan view which shows the rear-end face of the surgical instrument with a scope support member mounted thereon according to the seventh embodiment;

FIG. 18 is a perspective view which shows an overall configuration of joint forceps serving as a surgical instrument of the surgical system according to the seventh embodiment;

FIGS. 19 and 20 are diagrams for describing actions of the joint forceps serving as a surgical instrument of the surgical system according to the seventh embodiment;

FIG. 19 is a side view which shows the joint forceps with the manipulator-hand portion straight;

FIG. 20 is a side view which shows the joint forceps with the manipulator-hand portion turned in the first turning direction;

FIGS. 21 and 22 are diagrams for describing actions of the joint forceps serving as a surgical instrument of the surgical system according to the seventh embodiment;

FIG. 21 is a top view which shows the joint forceps with the manipulator-hand portion straight;

FIG. 22 is a top view which shows the joint forceps with the manipulator-hand portion turned in the second turning direction;

FIG. 23 is an explanatory diagram for describing actions of the forceps as to the sheath of the surgical instrument of the surgical system according to the seventh embodiment;

FIGS. 24 through 26 are diagrams for describing actions of an operation unit of the surgical instrument of the surgical system according to the seventh embodiment;

FIG. 24 is a front view which shows the entire operation unit supported in the normal state;

FIG. 25 is a front view which shows the entire operation unit turned counterclockwise from the normal state;

FIG. 26 is a front view which shows the entire operation unit turned clockwise from the normal state;

FIG. 27 is an explanatory diagram for describing actions wherein only the first forceps are turned around the axis thereof while maintaining the operation unit of the surgical instrument stationary (not rotated) according to the surgical system of seventh embodiment;

FIG. 28 is an explanatory diagram for describing actions wherein the first forceps are turned around the axis thereof as well as turning the operation unit of the surgical instrument according to the surgical system of the seventh embodiment;

FIG. 29 is an explanatory diagram for describing surgery wherein an electrocauterizer is inserted into the body of the patient through a surgical-instrument port of the sheath, using the surgical instrument of the surgical system according to the seventh embodiment; and FIG. 30 is an explanatory diagram for describing medical treatment of tissue in the body cavity using the surgical system according to the seventh embodiment.

DETAILED DESCRIPTION OF THE PREFERRED EMBODIMENTS

Figure 1:
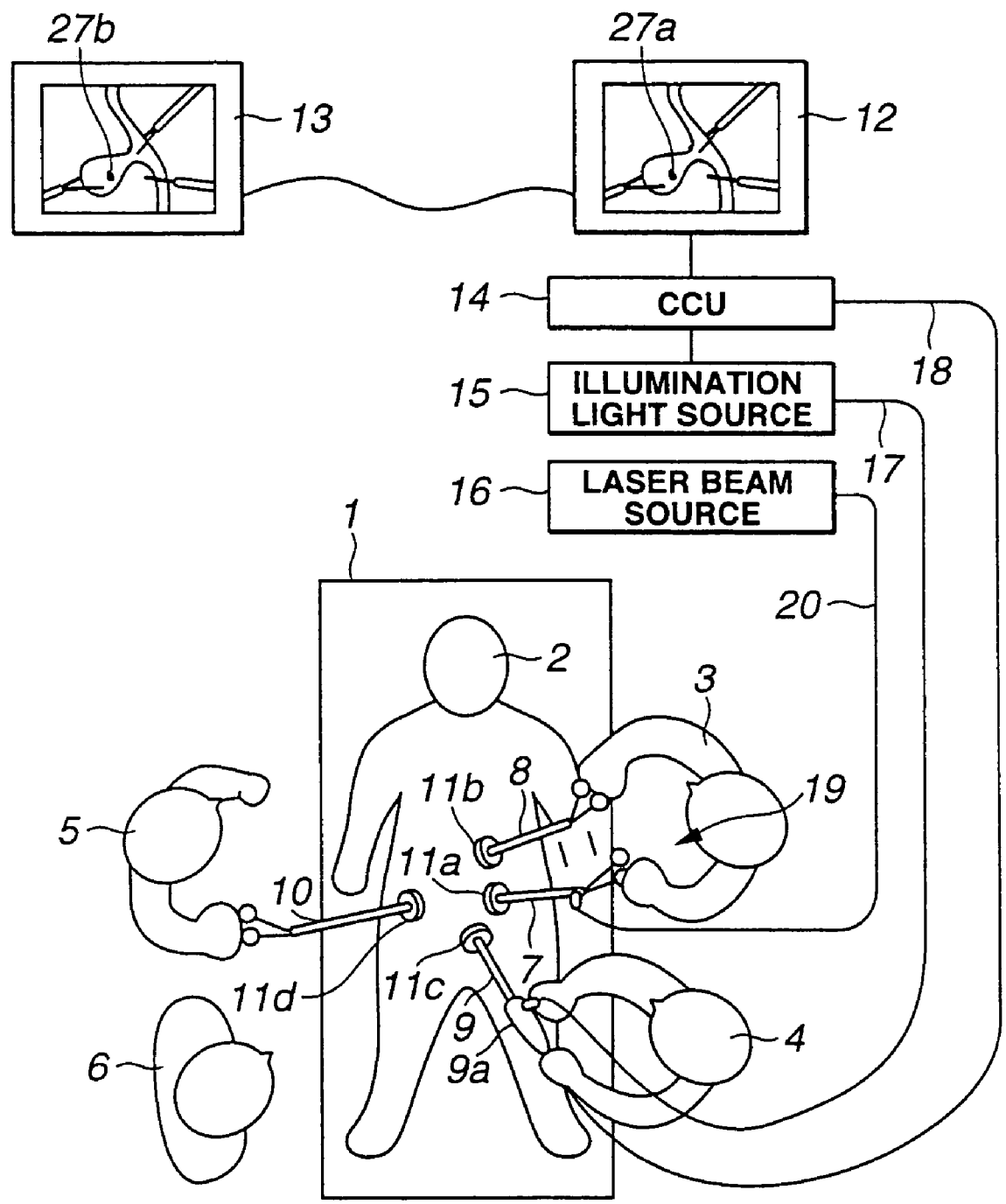
FIG. 1 is a diagram for describing surgery using an endoscopic surgical system according to a first embodiment of the present invention.

Description will be made below regarding a first embodiment according to the present invention with reference to FIGS. 1 through 3. FIG. 1 is a diagram for describing surgical treatment using an endoscopic surgical system. In FIG. 1, reference numeral 1 denotes a surgery table. A patient 2 lies on the surgery table 1. Multiple surgical staff members such as a surgeon 3, a first assistant 4, a second assistant 5, a nurse 6, and the like, take up positions around the surgery table so as to perform surgical treatment in cooperation with each other.

The surgeon 3 holds a first surgical instrument 7 in one hand and a second surgical instrument 8 in the other. For example, a laser forceps 19 is used as the first surgical instrument 7, and forceps are used as the second surgical instrument 8.

The first assistant 4 operates an endoscope 9 serving as an observing device for observing the portion which is to be subjected to surgical treatment. The second assistant 5 holds a third surgical instrument 10 for assisting the surgeon 3. Forceps are used as the third surgical instrument 10, for example.

Furthermore, a predetermined number of (four, in the present embodiment) trocars 11a through 11d are inserted through the abdominal wall of the patient 2 beforehand, corresponding to the number of the medical instruments of the endoscope 9 and the surgical instruments 7, 8, and 10. The endoscope 9 and the surgical instruments 7, 8, and 10 are inserted into insertion holes of tubes of the trocars 11a through 11d, respectively, whereby the endoscope 9 and the surgical instruments 7, 8, and 10, are inserted into the body of the patient 2 through the insertion holes of the trocars 11a through 11d.

Furthermore, two monitors serving as image display means, more specifically, a first monitor 12 and a second monitor 13 are installed near the surgery table 1 in the surgical room. Furthermore, a camera control unit (which will be referred to as "CCU" hereafter) 14, an illumination light source 15, and a laser beam source 16, are installed near the first monitor 12.

On the other hand, the endoscope 9 is connected to the illumination light source 15 through the illumination light transmission cable 17. This allows the illumination light source 15 to supply illumination light to the endoscope 9 through the illumination light source transmission cable 17.

Furthermore, the endoscope 9 includes a CCD camera unit 9a having a CCD (Charge Coupled Device) on the rear end thereof. The CCD camera unit 9a is connected to the camera control unit 14 through an electric cable 18. The camera control unit 14 is connected to the first and second monitors 12 and 13. This allows the first and second monitors 12 and 13 to display images of the portion taken by the endoscope 9, which is to be subjected to surgical treatment, on the screens thereof.

On the other hand, forceps having a laser emitting function (which will be referred to as "laser forceps" hereafter) 19 serving as the first surgical instrument 7 are connected to the laser beam source 16 through a laser transmission cable 20. The laser beam output from the laser beam source 16 is supplied to the laser forceps 19 through the laser transmission cable 20.

Figure 2:
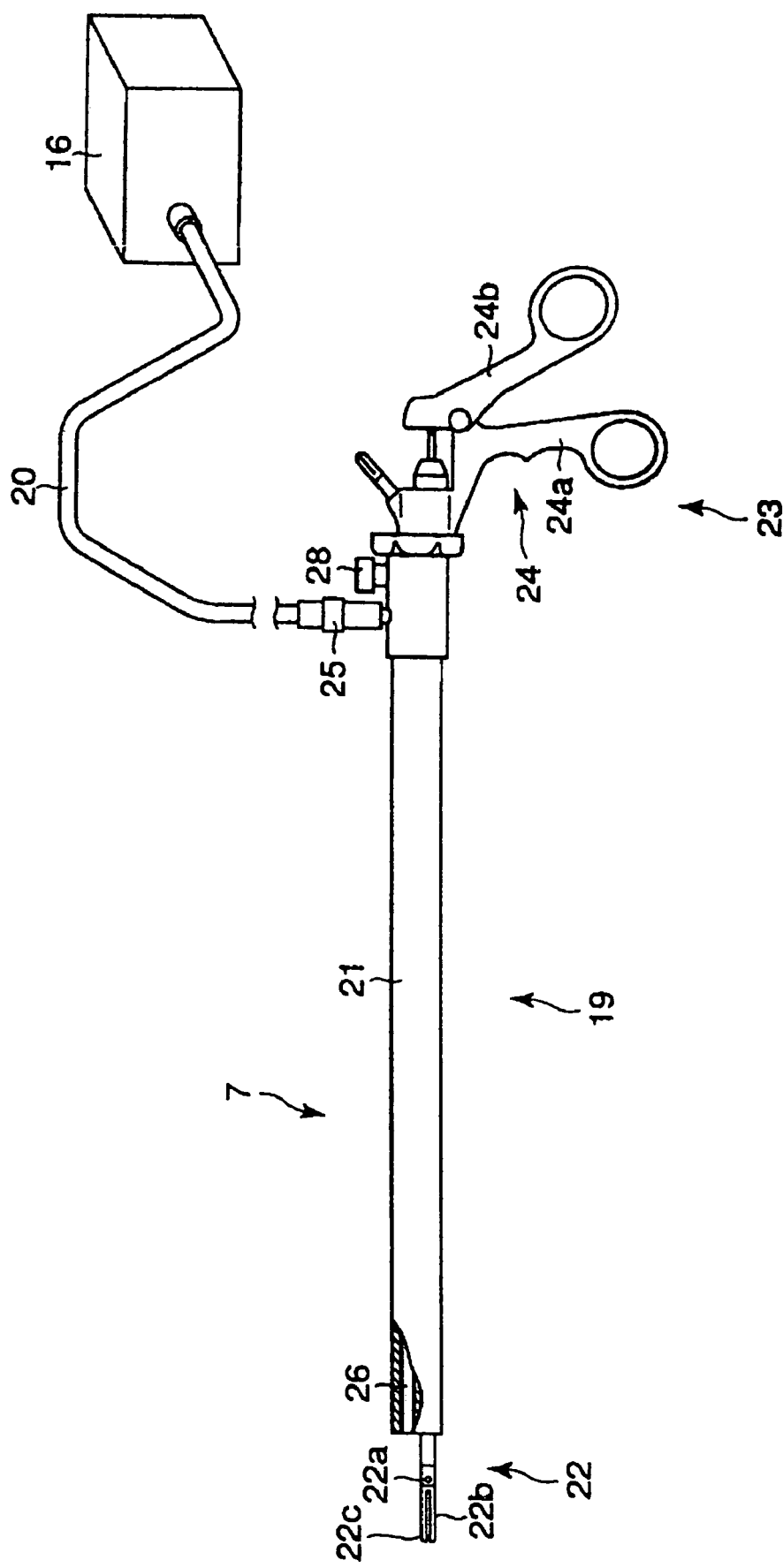
FIG. 2 is a schematic diagram which shows a configuration of laser forceps of the endoscopic surgical system according to the first embodiment.
Figure 3:
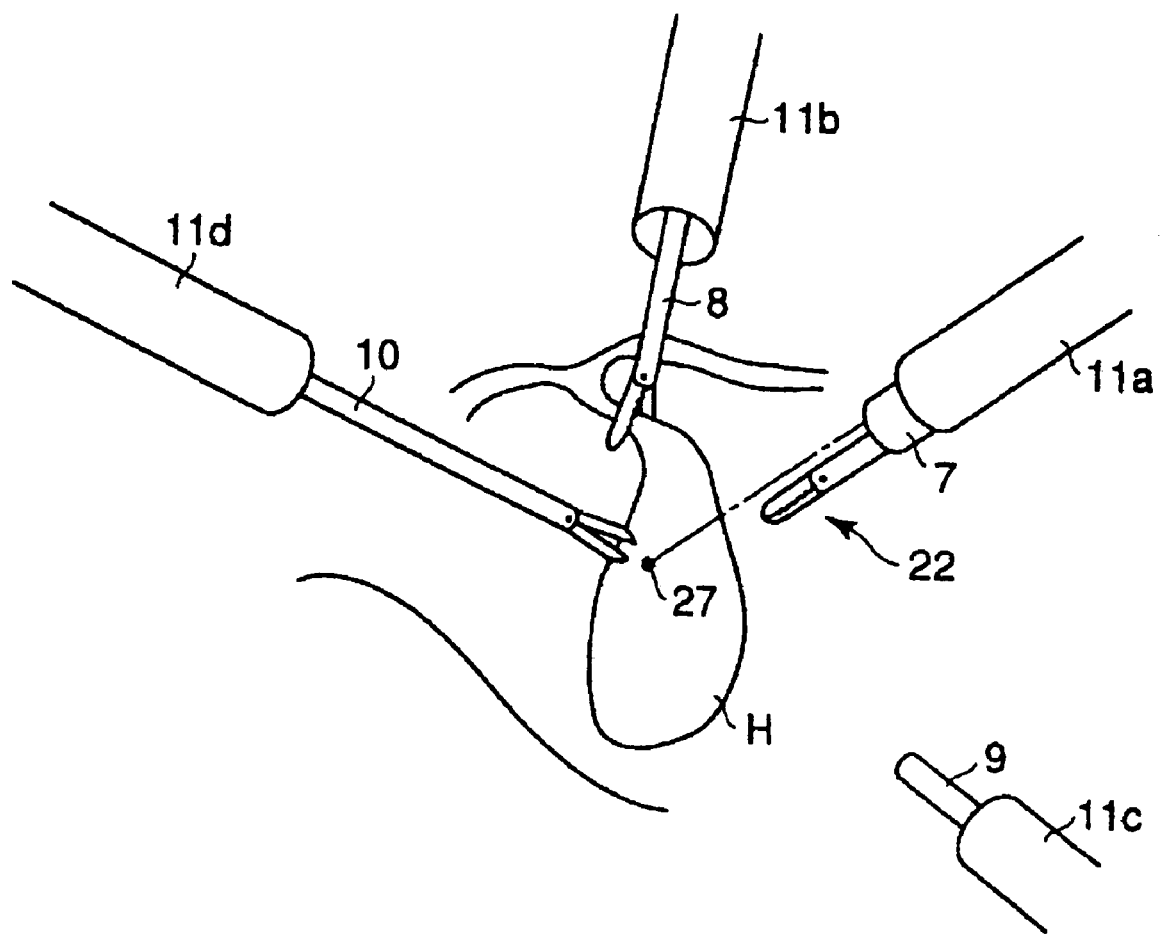
FIG. 3 is a diagram which shows medical treatment performed in the body cavity using the endoscopic surgical system according to the first embodiment.

FIG. 2 is a schematic diagram which shows a configuration of the laser forceps 19 having a long and narrow insertion portion 21 for being inserted into the body of the patient through a trocar 11a. The tip of the insertion portion 21 includes a support portion 22. Furthermore, the support portion 22 includes a pair of manipulator-hand members 22b and 22c turnably supported with a support shaft 22a as the axis thereof.

The base end of the insertion portion 21 includes an operation unit 23 for the surgeon. The operation unit 23 includes an operation handle 24. Furthermore, the operation handle 24 includes a fixed handle 24a and a movable handle 24b. Furthermore, the laser forceps have a mechanism wherein open/close control of the support portion 22 formed of the manipulator-hand members 22b and 22c can be performed by operating the operation handle 24.

Furthermore, a laser connector 25 is disposed so as to protrude on the outer face of the end of the insertion portion 21 toward the side of the operation unit 23. The laser connector 25 is connected to one end of the laser transmission cable 20. The other end of the laser transmission cable 20 is connected to the laser beam source 16.

Furthermore, the insertion portion 21 includes a laser optical fiber probe 26 formed of a laser optical fiber bundle therewithin. The tip of the laser optical fiber probe 26 is disposed at the tip face of the insertion portion 21. Furthermore, the base end of the laser optical fiber probe 26 is connected to the inner end of the laser connector 25. Thus, the laser beam propagating through the laser transmission cable 20 is supplied to the laser optical fiber probe 26, and the laser beam is emitted from the tip thereof. In this case, the laser forceps 19 have a configuration wherein a laser beam is brightly emitted from the tip thereof so as to illuminate a spot of tissue of the body cavity (indicating point 27 in FIG. 3). Furthermore, the spot of the tissue in the body cavity illuminated with the laser beam emitted from the tip of the laser forceps 19 can be observed as indicating points 27a and 27b on the first and second monitors 12 and 13. Thus, the laser optical fiber probe 26 disposed at the tip face of the insertion portion 21 serves as indicating-point forming means for forming an indicating point serving as an indicator of a point, more generally referred to as a pointer.

Furthermore, the operation unit 23 of the laser forceps 19 includes a switch 28 for emitting a laser beam, wherein the user can perform on/off control of laser beam emission by operating the switch 28. Thus, the laser forceps 19 according to the present embodiment serves as laser beam positioning means for controlling the position of the indicating point 27 formed of a laser-beam spot.

Next, description will be made regarding operations of the above-described configuration. FIG. 3 is a diagram which shows medical treatment performed within the body cavity using the endoscopic surgical system according to the present embodiment. At the time of use of the endoscopic surgical system according to the present embodiment, the surgeon operates the laser forceps 19 serving as the first surgical instrument 7 and forceps serving as the second surgical instrument 8 so as to be inserted into the body cavity through the trocars 11a and 11b, respectively. In the same way, the assistant 4 operates the endoscope 9 so as to be inserted into the body cavity through the trocar 11c.

Furthermore, the second assistant 5 operates forceps serving as the third surgical instrument 10 so as to be inserted within the body cavity through the trocar 11d.

Subsequently, the endoscope 9 allows the surgical staff members to observe tissue H in the body cavity, and the surgical instruments 7, 8, and 10, which are operated by the surgical staff members. At this time, the surgeon 3 can perform on/off control of laser beam emission by operating the switch 28 of the laser forceps 19. Upon the surgeon 3 turning on the switch 28, a laser beam is emitted from the tip of the laser forceps 19. As a result, the laser beam forms a bright laser beam spot on the surface of the tissue in the body cavity. Thus, the surgeon can form the indicating point 27 formed of a laser beam spot serving as an indicator at a desired portion on the surface of the tissue in the body cavity by operating the laser forceps 19.

Thus, the indicating point 27 formed by the surgeon 3 can be observed through the endoscope 9. Thus, the surgical staff members such as the first and second assistants 4 and 5, the nurse 6, and so forth, can confirm the indicating point 27 within the body cavity, pointed by the surgeon 3 through observation of the indicating points 27a and 27b in endoscopic images displayed on the first and second monitors 12 and 13.

Thus, the endoscopic surgical system having such a configuration has advantages as follows. That is to say, with the endoscopic surgical system according to the present embodiment, the laser forceps 19 serving as the first surgical instrument 7 include the laser beam optical fiber probe 26 within the insertion portion 21 thereof. Accordingly, the surgeon 3 can use the laser forceps 19 as indicating-point forming means for forming the indicating point 27 at a desired point on the tissue surface of the body cavity using a laser beam emitted from the laser forceps 19, as well as using this as forceps.

On the other hand, the surgical staff members such as the first and second assistants 4 and 5, the nurse 6, and so forth, can precisely confirm the indicating point 27 pointed by the surgeon 3 through observation of the indicating points 27a and 27b displayed on the first and second monitors 12 and 13. Thus, the surgeon 3 can use the laser forceps 19 as indicating-point forming means for forming the indicating point 27 at a desired portion on the tissue surface in the body cavity for other surgical staff members. Thus, the endoscopic surgical system according to the present embodiment facilitates communication between the surgeon 3 and other surgical staff members in a case of medical treatment performed by multiple surgical staff members under endoscopic observation, thereby reducing a period of time for medical treatment, and reducing the load on the surgical staff members.

Furthermore, with the present embodiment, a laser beam is used as indicating-point forming means for forming an indicating point, and accordingly, the endoscopic surgical system according to the present embodiment has the advantage of forming an indicating point at a desired portion with excellent precision even in the event that direct access of the tip of the forceps 19 to the desired portion is difficult. Thus, the surgeon 3 can precisely indicate a desired position on the tissue surface in the body cavity by forming the indicating point 27 for other surgical staff members as compared with a case wherein the surgeon 3 indicates the desired position using the tip of the forceps without a laser spot.

Furthermore, the surgeon 3 can easily and precisely transmit this crucial information as compared with a case wherein the surgeon 3 transmit this crucial information only through conversation, thereby reducing error of communication between surgical staff members, and reducing the load thereof.

Furthermore, the surgical staff members can confirm the direction of the forceps 19 through observation of the position of the indicating points 27 formed of a laser beam spot, even if the laser forceps 19 is outside of the screen. This facilitates other surgical staff members to follow actions performed by the surgeon 3.

Note that in the present embodiment, while description has been made regarding an arrangement wherein the surgeon 3 operates the laser forceps 19, the operator of a laser forceps is not restricted to the surgeon 3, rather, an arrangement may be made wherein the second assistant 5 operates a laser forceps serving as the third surgical instrument 10 so as to instruct other surgical staff members in the same way.

Figure 4:
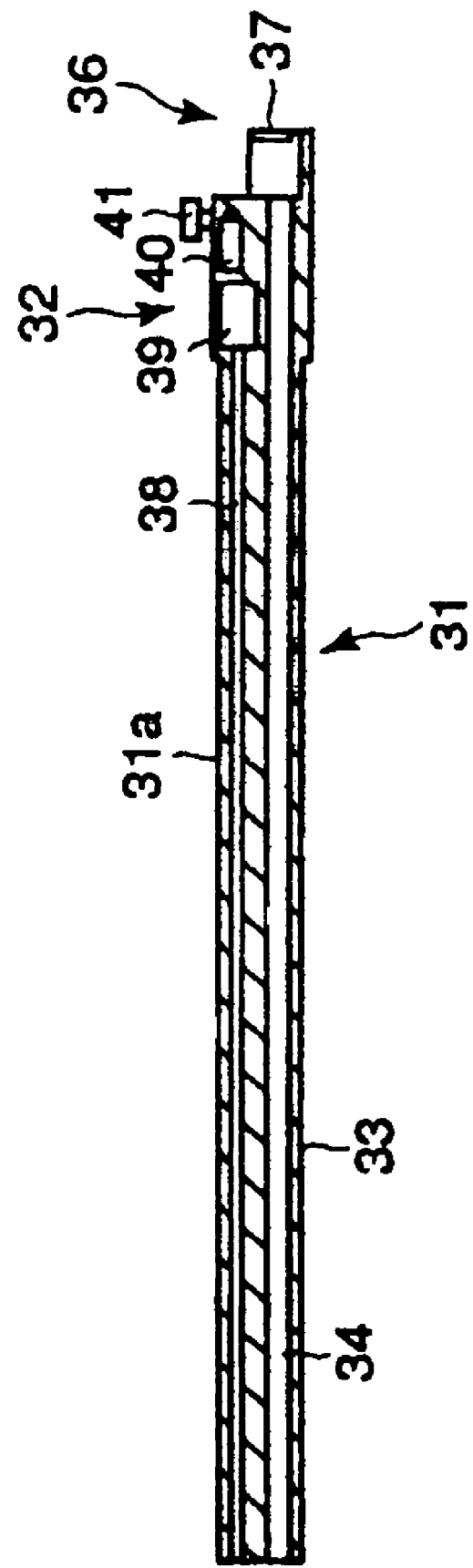
FIGS. 4 and 5 are diagrams for describing indicating-position forming means for forming an indicating point according to a second embodiment of the present invention.
Figure 5:
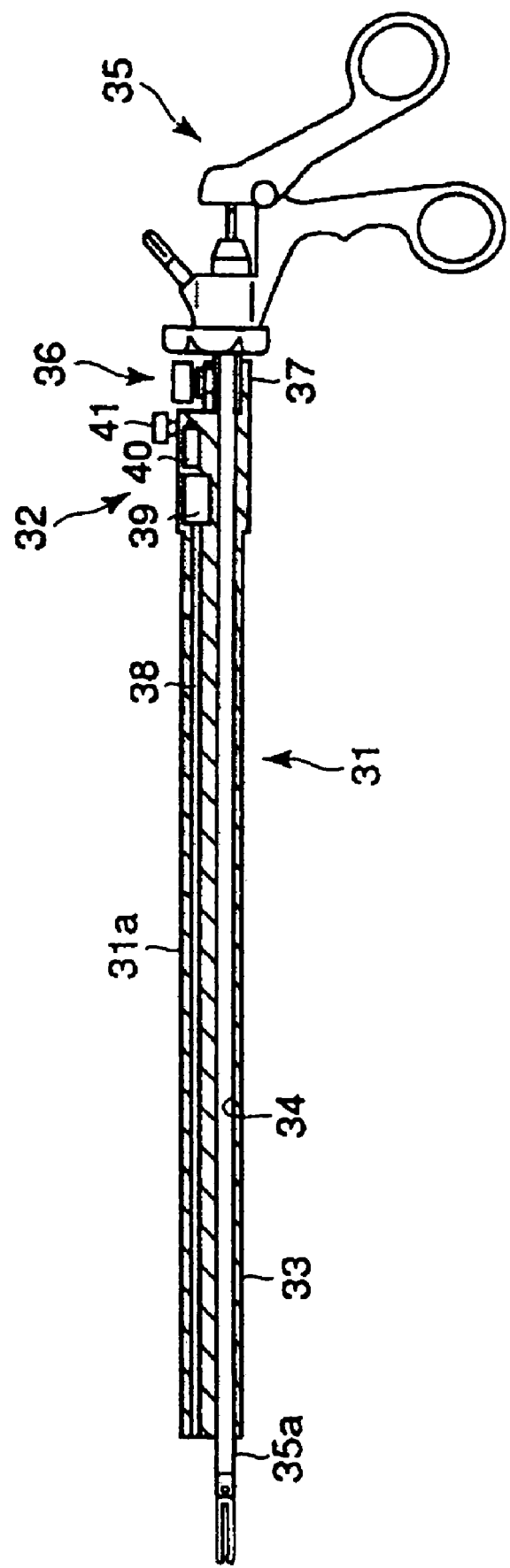

Next, description will be made regarding a second embodiment according to the present invention with reference to FIGS. 4 and 5. While description has been made in the first embodiment (see FIGS. 1 through 3) regarding indicating-point forming means having a configuration wherein the laser forceps 19 serving as the first surgical instrument 7 includes the laser optical fiber probe 26 within the insertion portion 21 thereof for forming the indicating point 27 formed of a laser beam spot at a desired position, indicating-point forming means according to the present embodiment has a configuration wherein a long and narrow forceps holder 31 includes indicating-point forming means 32 for forming the indicating point 27 at a desired position as shown in FIG. 4. Thus, with the present embodiment, the forceps holder serves as indicating-point forming means for forming the indicating point 27 of laser beam spot at a desired position.

With the forceps 31 according to the present embodiment, a main body 31a thereof is formed of an sheath 33. The sheath 33 includes forceps insertion hole 34 for inserting forceps 35, serving as a through hole along the axial direction thereof, as shown in FIG. 5.

Furthermore, the sheath 33 includes forceps holder 36 on the base end thereof. The forceps holder 36 includes engaging means 37 for detachably mounting the base end of an insertion portion 35a of the forceps 35 to the sheath 33 upon the surgeon inserting the insertion portion 35a of the forceps 35 into the forceps insertion hole 34.

Furthermore, the sheath 33 includes a laser optical fiber probe 38 therein extending parallel to the forceps insertion hole 34, i.e., along the axial direction. Note that the tip of the laser optical fiber probe 38 extends up to the tip of the sheath 33. Furthermore, the base end of the laser optical fiber probe 38 includes a laser oscillation unit 39 formed of a semiconductor laser unit and a driving unit thereof. The laser oscillation unit 39 is included within the base end of the sheath 33. A laser beam emitted from the laser oscillation unit 39 propagates to the tip of the sheath 33 through the laser optical fiber probe 38, whereby the laser beam is emitted from the tip of the sheath 33.

Furthermore, the base end of the sheath 33 includes a battery 40 therewithin. The battery 40 is included for supplying energy to the laser oscillation unit 39 for laser oscillation. Furthermore, the base end of the sheath 33 includes a switch 41 for on/off control of laser beam emission. The switch 41 allows the surgeon to perform on/off control of laser beam emission.

Next, description will be made regarding operations of the present embodiment having such a configuration. FIG. 5 is a partially-cross-sectional view which shows the laser forceps holder 31 with the forceps 35 mounted thereon. Description will be made regarding operations of the laser forceps holder with reference to FIG. 5. With the present embodiment, let us say that the surgeon 3 uses the surgical instrument of the laser forceps holder 31 mounting the forceps 35 serving as the first surgical instrument 7. In this case, the forceps 35 is fixed to the laser forceps holder 31, and accordingly, the forceps 35 and the laser forceps holder 31 are operated as a single unit. Thus, the surgeon controls the direction of laser beam emission by adjusting the direction of the insertion unit 35a of the forceps 35. The surgeon 3 inserts the surgical instrument of the laser forceps holder 31 mounting the forceps 35 into the body cavity through the trocar 11a, following which the surgeon 3 can indicates a desired position on the tissue surface in the body cavity using a laser beam emitted from the tip of the laser optical fiber probe 38 of the laser forceps holder 31.

In this case, the indicating point serving as the indicator pointed by the surgeon 3 is observed through the endoscope 9. Thus, the surgical staff members such as the first and second assistants 4 and 5, the nurse 6, and so forth, can confirm the indicating point 27 pointed by the surgeon 3 through observation of the indicating points 27a and 27b displayed in endoscopic images on the first and second monitors 12 and 13.

That is to say, with the endoscopic surgical system according to the present embodiment, the surgeon 3 can indicate a desired position on the tissue surface in the body cavity as the indicating point 27 using a laser beam emitted from the forceps holder 31 mounted on the forceps 35, which is operated by the surgeon 3. On the other hand, the surgical staff members such as the first and second assistants 4 and 5, the nurse 6, and so forth, confirm the indicating points 27a and 27b displayed on the first and second monitors 12 and 13, thereby enabling the surgical staff members to follow the precise position of the indicating point 27 pointed by the surgeon 3.

Thus, the laser forceps holder 31 according to the present embodiment may be employed as indicating-point forming means for forming the indicating point 27 at a desired position on the tissue surface in the body cavity for other surgical staff members. As a result, in the same way as with the first embodiment, this facilitates communication between the surgeon 3 and other surgical staff members, thereby enabling smooth surgical treatment, and thereby reducing the load of the surgical staff members, as well as reducing a period of time for surgical treatment, in a case of surgical treatment by multiple surgical staff members under endoscopic observation.

Furthermore, in addition to the advantages of the first embodiment, the endoscopic surgical system according to the present embodiment further has advantages as follows. That is to say, the laser forceps holder 31 includes the laser oscillation unit 39 for supplying a laser beam to the laser optical fiber probe 38 and the battery 40 therewithin, and accordingly, no cables or the like extend outside of the laser forceps holder 31, unlike the endoscopic surgical system according to the first embodiment wherein the laser transmission cable 20 and the like extend therefrom, thereby enabling a simple layout around the surgery table.

Furthermore, with the present embodiment, the surgeon 3 can select a desired pair of forceps from multiple forceps so as to be mounted on the single laser forceps holder 31, thereby enabling a desired combination of the forceps and the laser forceps holder 31 to be formed as necessary.

Figure 6:
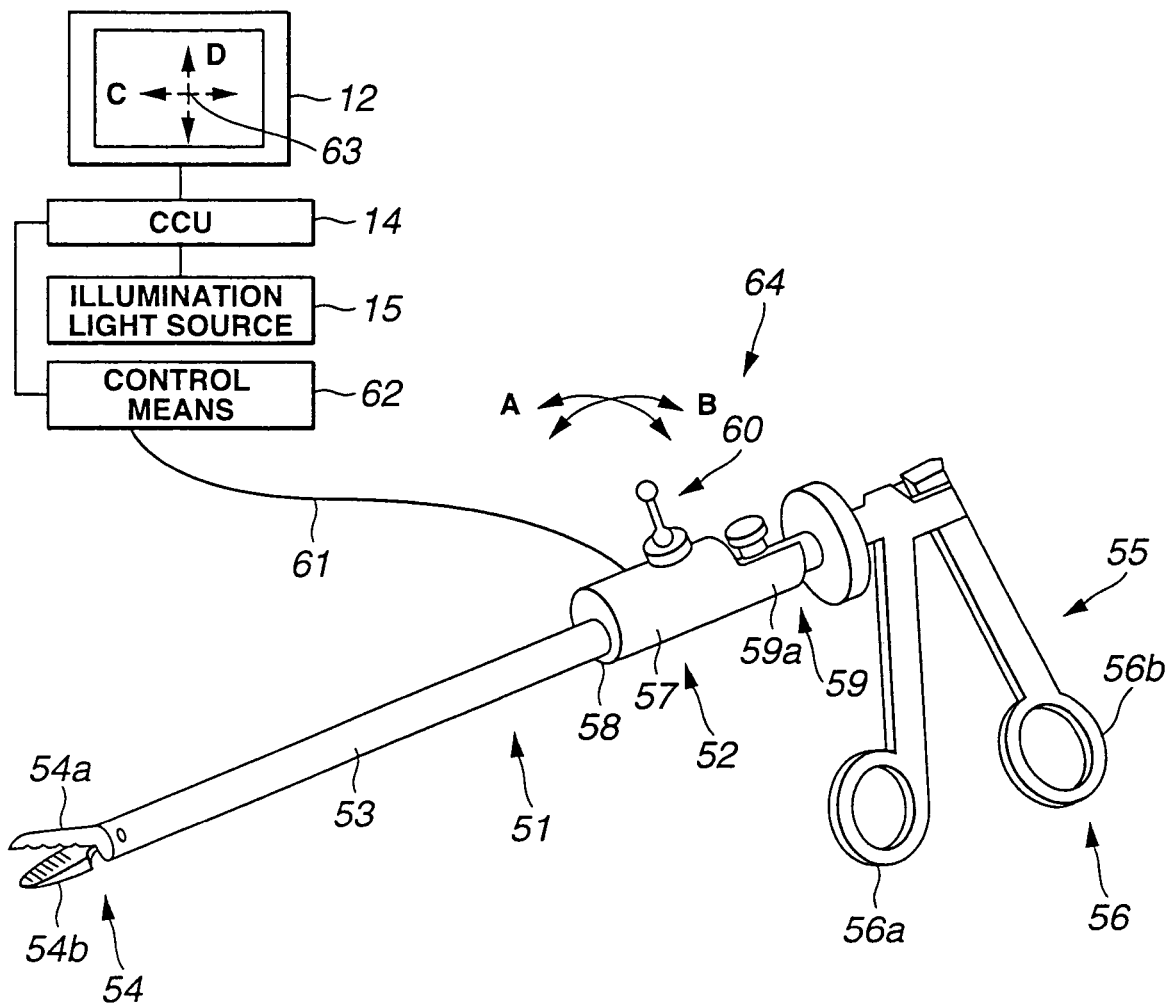
FIGS. 6 and 7 are diagrams for describing a third embodiment of the present invention.
Figure 7:
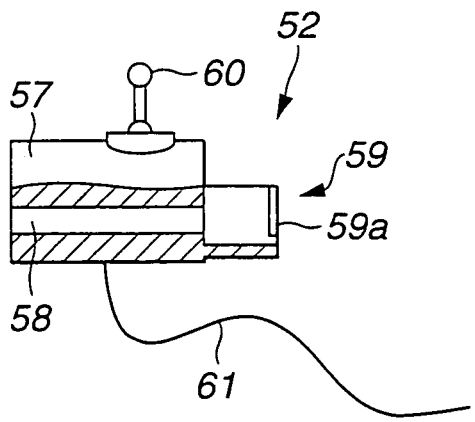

Next, description will be made regarding a third embodiment according to the present invention with reference to FIGS. 6 and 7. FIG. 6 is a diagram for describing indicating-point superimposing means according to the third embodiment of the present invention. FIG. 7 is a partially cross-sectional view which shows a joy-stick unit according to the third embodiment of the present invention. An endoscopic surgical system according to the present embodiment includes indicating-point superimposing means 64 wherein the surgeon can control the position of an indicating point 63 serving as an indicator displayed on the screens of the monitors 12 and 13 by operating a joy-stick device 60, instead of the indicating-point forming means according to the first embodiment (see FIGS. 1 through 3) which allows the surgeon to form the indicating point 27 formed of a laser beam spot at a desired position on the tissue surface in the body cavity. Note that the same components as with the first embodiment are denoted by the same reference numerals, and description thereof will be omitted.

That is to say, with the present embodiment, a joy-stick unit 52 is detachably mounted to forceps 51 as shown in FIG. 6. With such a configuration, the forceps 51 includes a long and narrow insertion portion 53. Furthermore, the insertion portion 53 comprises a manipulator-hand portion 54 on the tip thereof. The manipulator-hand portion 54 includes a pair of manipulator-hand members 54a and 54b supported thereby so as to be capable of opening and closing.

Furthermore, the base end of the insertion portion 53 includes an operation unit 55 for the surgeon. The operation unit 55 includes an operation handle 56. The operation handle 56 comprises a fixed handle 56a and a movable handle 56b. The surgeon can perform open/close control of the manipulator-hand portion 54 formed of the manipulator-hand members 54a and 54b by operating the operation handle 56.

On the other hand, the unit main body of the joy-stick unit 52 includes an sheath 57. The sheath 57 includes forceps through hole 58 along the axial direction thereof as shown in FIG. 7. The forceps through hole 58 is included for inserting the insertion portion 53 of the forceps 51.

The base end of the sheath 57 includes forceps holding portion 59. The forceps holding portion 59 includes engaging means 59a for detachably mounting the base end of the insertion portion 53 of the forceps 51 to the sheath 57 upon the surgeon inserting the insertion portion 53 of the forceps 51 into the forceps insertion hole 58. Thus, at the time of mounting the joy-stick unit 52 to the forceps 51, the surgeon inserts the insertion portion 53 of the forceps 51 into the forceps through hole 58 of the sheath 57, and the joy-stick 52 is fixed to the forceps 51 with the forceps holding portion 59 of the joy-stick unit 52.

Furthermore, the joy-stick device 60 is disposed on the outer face of the sheath 57. Upon the surgeon mounting the joy-stick unit 52 to the forceps 51, the joy-stick device 60 is disposed near the operation unit 55 of the forceps 51.

Furthermore, the joy-stick unit 52 is connected to control means 62 through an electric cable 61. With such a configuration, the input signals from the joy-stick unit 52 are transmitted to the control means 62 through the electric cable 61.

The control means 62 is connected to the camera control unit 14. Each of the monitors 12 and 13 displays the indicating point 63 on the screens thereof according to control signals output from the control means 62. The surgeon can control the position of the indicating point 63 displayed on the screens of the monitors 12 and 13 by operating the joy-stick device 60. Thus, indicating-point superimposing means 64 according to the present embodiment is formed of the joy-stick unit 52, the forceps 51 to which the joy-stick unit 52 is mounted and the control means 62.

Next, description will be made regarding operations of the present embodiment having such a configuration. At the time of use of the endoscopic surgical system according to the present embodiment, the surgeon 3 uses the forceps 51 with the joy-stick unit 52 mounted thereon as shown in FIG. 6. The surgeon 3 can control the position of the indicating point 63 displayed on the screens of the monitors 12 and 13 by operating the lever of the joy-stick device 60 while holding the operation unit 55 of the forceps 51. In this case, upon the surgeon operating the joy-stick device 60 such that the lever thereof is tilted in the first direction denoted by arrow A in FIG. 6, in the second direction denoted by arrow B in the same drawing orthogonal to the first direction, and in desired directions other than the first and second directions, the indicating point 63 displayed on the first monitor 12 moves in the first direction denoted by arrow C in FIG. 6, in the second direction denoted by arrow D in the same drawing orthogonal to the first direction, and in desired directions other than the first and second directions.

Furthermore, the first monitor 12 displays observation images taken by the endoscope 9 on the screen thereof as shown in FIG. 1. With the present embodiment, the indicating point 63 is superimposed on the observation image, and thus, the surgeon 3 can indicates a desired position on the tissue in the body cavity observed through the endoscope 9 using the indicating point 63 controlled by operating the joy-stick device 60. Note that the second monitor 13 displays the same image on the screen thereof as with the first monitor 12.

With the present embodiment, the indicating point 63 indicated by the surgeon 3 is displayed on the first and second monitors 12 and 13, and accordingly, the surgical staff members such as the first and second assistants 4 and 5, the nurse 6, and so forth, can confirm the position of the indicating point 63, thereby allowing the surgical staff members to follow the precise position of the indicating point 63 indicated by the surgeon 3.

Thus, the image-point display means according to the present embodiment having such a configuration has advantages as follows. That is to say, with the present embodiment, the surgeon 3 can use the forceps 51 with the joy-stick unit 52 mounted thereto serving as the indicating-point superimposing means 64 for allowing the surgeon to indicate a desired position on the tissue in the body cavity for other surgical staff members.

Furthermore, with the aforementioned configuration, the joy-stick device 60 is disposed near the operation unit 55 of the forceps 51, and thus, the surgeon 3 can operates both the forceps 51 and the joy-stick device 60 with one hand.

Furthermore, with the present embodiment, the surgeon 3 can position the indicating point 63 on the monitor 12 at a desired position by operating the joy-stick device 60, regardless of the direction of the forceps 51. Thus, the surgeon can indicate a desired position even while performing surgical treatment with the forceps 51.

Note that the operator of the indicating-point superimposing means 64 is not restricted to the surgeon 3, rather, an arrangement may be made wherein the second assistant 5 operates the indicating-point superimposing means 64 so as to instruct other surgical staff members.

Next, description will be made regarding a fourth embodiment according to the present invention with reference to FIG. 8. The endoscopic surgical system according to the present embodiment includes indicating-point forming means having a configuration modified based upon the configuration of the indicating-point forming means for forming the indicating point 27 of a laser beam spot according to the first embodiment (see FIGS. 1 through 3). Note that the same components as with the first embodiment are denoted by the same reference numerals, and description thereof will be omitted.

Figure 8:
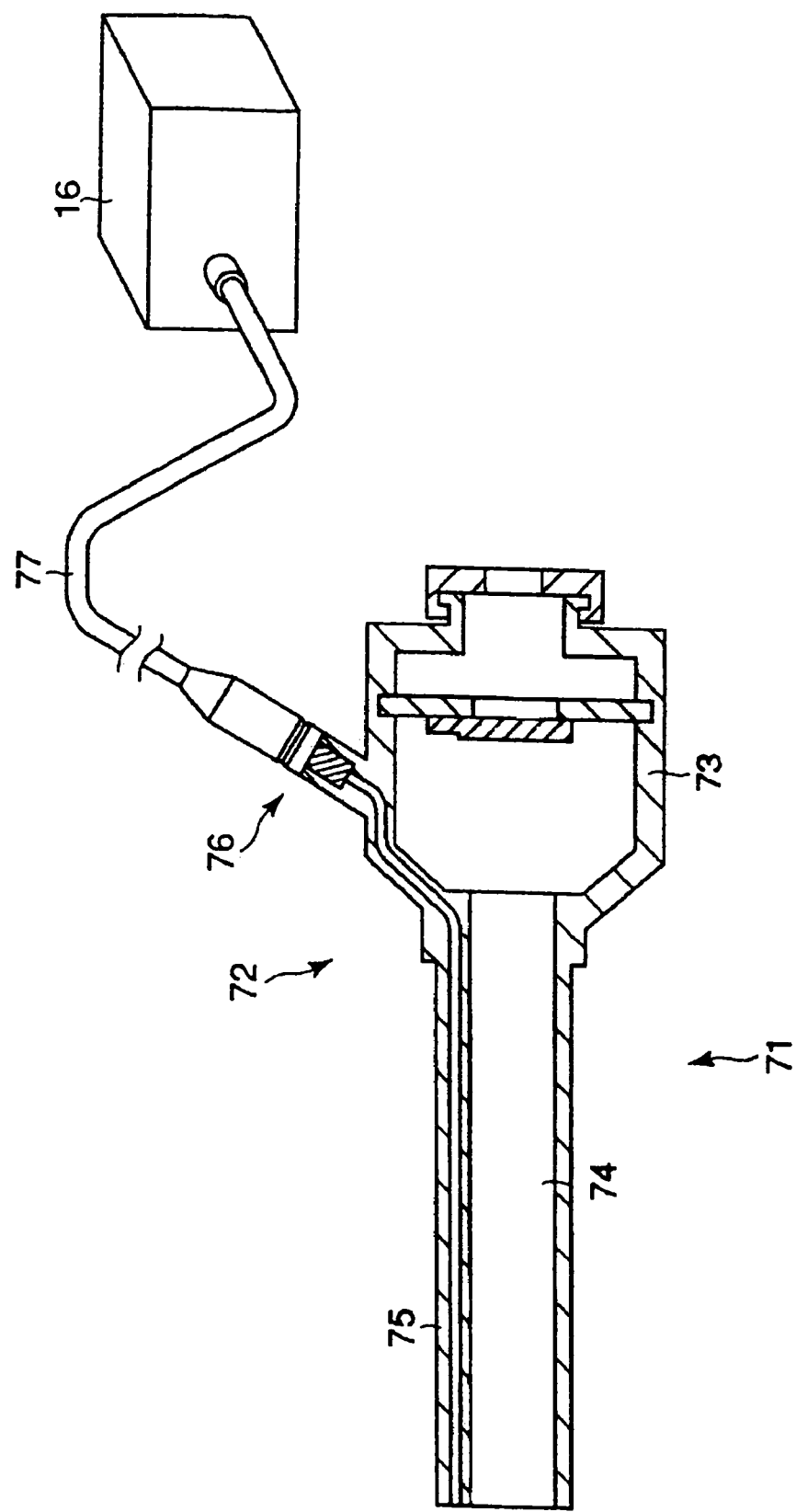
FIG. 8 is an explanatory diagram for describing a configuration of indicating-point forming means for forming an indicating point of a surgical system according to a fourth embodiment of the present invention.

That is to say, indicating-point forming means 72 comprise a trocar unit 71 and the laser beam source 16 as shown in FIG. 8. The unit main body of the trocar unit 71 includes an sheath 73.

The sheath 73 includes an insertion hole 74 for inserting a surgical instrument. Furthermore, the sheath 73 includes a laser optical fiber probe 75 therewithin extending along the axial direction. The tip of the laser optical fiber probe 75 is disposed at the tip face of the sheath 73. Furthermore, the base end of the laser optical fiber probe 75 is connected to the inner end of a laser connector 76 disposed on the base end of the sheath 73. The other end of the laser connector 76 disposed on the sheath 73 is connected to a laser transmission cable 77. The other end of the laser transmission cable 77 is connected to the laser beam source 16. With such a configuration, a laser beam supplied from the laser beam source 16 is emitted from the tip face of the laser optical fiber probe 75.

Next, description will be made regarding operations of the indicating-point forming means having such a configuration. With the present embodiment, the surgeon 3 inserts the surgical instrument into the insertion hole 74 of the trocar unit 71. Then, upon the surgeon 3 operating the surgical instrument, the trocar unit 71 is integrally moved with the surgical instrument such that the axial direction of the sheath 73 matches the axial direction of the surgical instrument inserted into the insertion opening 74. Thus, the surgeon 3 can integrally move the trocar unit 71 by operating the surgical instrument, thereby allowing the surgeon 3 to control the direction of a laser beam emitted from the laser optical fiber probe 75 of the trocar unit 71 by operating the surgical instrument. Thus, the surgeon 3 can indicate a desired position on the tissue which is to be subjected to medical treatment using a laser beam by controlling the surgical instrument.

In this case, an indicating point indicated by the surgeon 3 is observed through the endoscope 9, and observation images are displayed on the first and second monitors 12 and 13. This allows the surgical staff members such as the first and second assistants 4 and 5, the nurse 6, and so forth, to confirm the position of the indicating point, and thus, the surgical staff members can follow the precise position of the indicating point indicated by the surgeon 3.

Thus, the endoscopic surgical system according to the present embodiment having such a configuration has advantages as follows. That is to say, the indicating-point forming means 72 according to the present embodiment is formed of the trocar unit 71 and the laser beam source 16, thereby allowing the surgeon 3 to indicate a desired position on the tissue in the body cavity for other surgical staff members by operating the surgical instrument inserted into the insertion hole 74 of the trocar unit 71.

With the indicating-point forming means 72 according to the present embodiment, an indicating point is formed using a laser beam, and accordingly, the surgeon can precisely indicate any desired position in the body cavity as long as the tip of the sheath 73 of the trocar unit 71 is in line of view of the desired position so as to cast a laser beam emitted from the laser optical fiber probe 75 of the trocar unit 71 thereonto.

Furthermore, with the present embodiment, even in a case of the surgical instrument inserted into the trocar unit 71 being outside of the screens of the monitors 12 and 13, the surgical staff members can confirm the direction of the surgical instrument through observation of the position of the laser beam spot, thereby facilitating the surgical staff members to follow actions performed by the surgeon 3.

Furthermore, with the present embodiment, the indicating point is formed using a laser beam emitted from the trocar unit 71, and various kinds of surgical instruments, which are used through a conventional trocar, can be inserted into the sheath 73 of the trocar unit 71 so as to be used in combination with the trocar unit 71 according to the present embodiment. Thus, various kinds of surgical instruments, which are used through a conventional trocar, can be used through the trocar unit 71 according to the present embodiment as the indicating-point forming means 72 by inserting a desired surgical instrument into the sheath 73.

Note that the operator of the trocar unit 71 according to the present embodiment is not restricted to the surgeon 3, rather, other surgical staff members such as the first and second assistants 4 and 5, the nurse 6, and so forth, may use the trocar unit 71. For example, the second assistant 5 may use the trocar unit 71 so as to instruct other surgical staff members.

Figure 9:
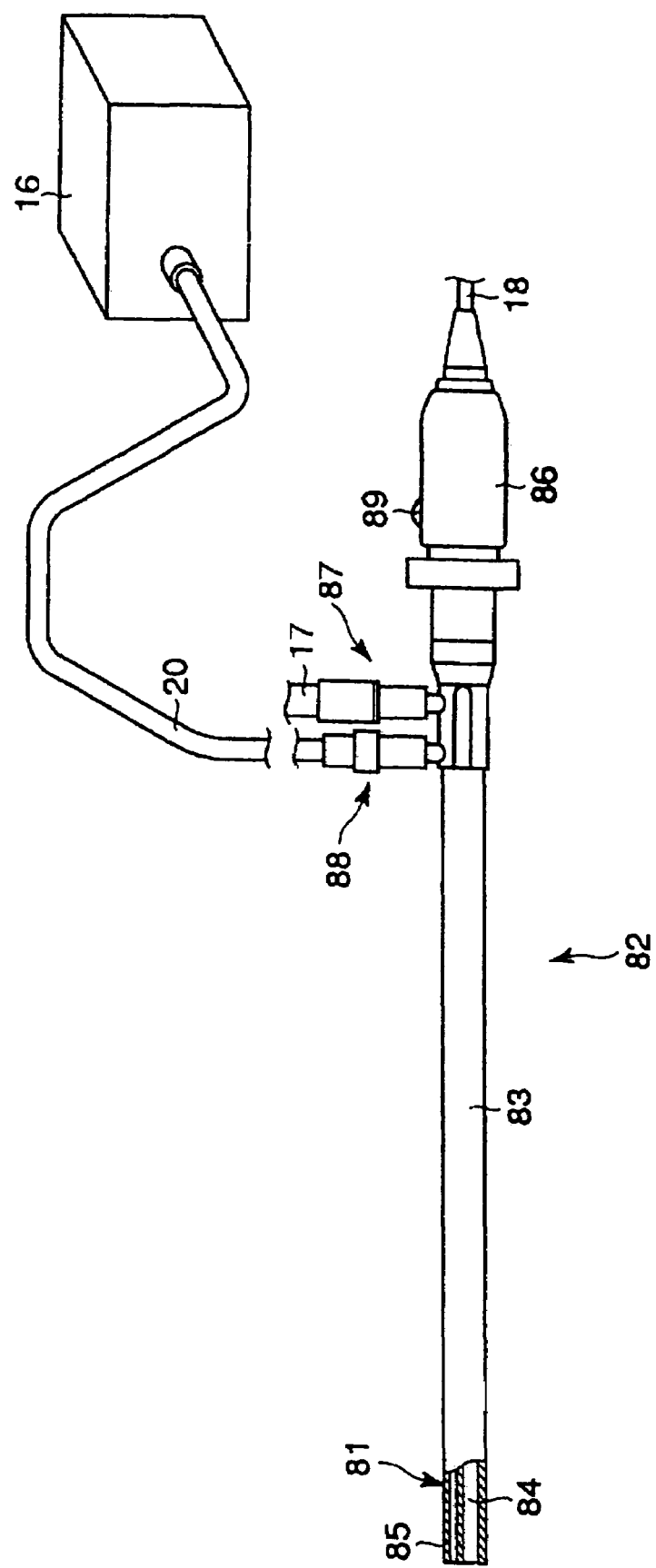
FIG. 9 is an explanatory diagram for describing a configuration of indicating-point forming means for forming an indicating point of a surgical system according to a fifth embodiment of the present invention.

Next, description will be made regarding a fifth embodiment according to the present invention with reference to FIG. 9. The endoscopic surgical system according to the present embodiment includes indicating-point forming means having a configuration modified based upon the configuration of the indicating-point forming means for forming the indicating point 27 of a laser beam spot according to the first embodiment (see FIGS. 1 through 3) as follows.

That is to say, with the endoscopic surgical system according to the present embodiment, the endoscope 9 includes an endoscopic unit 82 having indicating-point forming means 81. The endoscopic unit 82 includes a narrow and long insertion portion 83. The insertion portion 83 includes an optical unit 84 formed of optical components such as a lens and the like, an optical fiber probe 85, and an unshown light guide for an optical fiber cable.

Furthermore, a CCD camera unit 86 is mounted on the base end of the insertion portion 83. An observation image formed by the optical unit 84 is focused on an imaging face of an unshown CCD of the CCD camera unit 86, and the observation image is taken by the CCD camera unit 86.

The CCD camera unit 86 is connected to one end of the electric cable 18. On the other hand, the other end of the electric cable 18 is connected to the camera control unit 14 shown in FIG. 1. Accordingly, observation images taken by the optical unit 84 are displayed on the first and second monitors 12 and 13.

The base end of the insertion portion 83 includes an illumination light connector 87 and a laser connector 88 so as to protrude on the outer face thereof. The inner end of the illumination light connector 87 is connected to the base end of an unshown optical fiber cable. The tip of the optical fiber cable extends up to the tip of the insertion portion 83.

On the other hand, the outer end of the illumination light connector 87 is connected to one end of the illumination light transmission cable 17. On the other hand, the other end of the illumination light transmission cable 17 is connected to the illumination light source 15 as shown in FIG. 1. Illumination light supplied from the illumination light source 15 is transmitted to the light guide of the unshown fiber cable through the illumination light transmission cable 17 so as to illuminate tissue in the body cavity with illumination light emitted from the tip of the endoscope unit 82.

Furthermore, the inner end of the laser connector 88 is connected to the base end of the optical fiber probe 85. Note that the tip of the optical fiber probe 85 extends up to the tip of the insertion portion 83. On the other hand, the outer end of the laser connector 88 is connected to one end of the laser transmission cable 20. On the other hand, the other end of the laser connector 88 is connected to the laser beam source 16. With such a configuration, a laser beam supplied from the laser beam source 16 through the laser transmission cable 20 is supplied to the laser optical fiber probe 85, whereby the laser beam is emitted from the tip face of the laser optical fiber probe 85.

Furthermore, a switch 89 for on/off control of laser beam emission is disposed on the outer face of the CCD camera unit 86. The surgeon can perform on/off control of laser beam emission by operating the switch 89. Thus, the indicating-point forming means 81 for forming an indicating point of a laser beam spot according to the present embodiment comprises the endoscope unit 82 and the laser beam source 16.

Next, description will be made regarding operations of the present embodiment having such a configuration. At the time of use of the endoscopic surgical system according to the present embodiment, the first assistant 4 may operate the endoscope unit 82 so as to indicate a desired position on the tissue in the body cavity using a laser beam emitted from the endoscope unit 82.

In this case, the indicating point indicated by the first assistant 4 who operates the endoscope unit 82 can be observed through the optical unit 84. At the same time, the surgical staff members other than the first assistant 4, such as the surgeon 3, the second assistant 5, the nurse 6, and so forth, can observe the indicating point in endoscopic images displayed on the first and second monitors 12 and 13, thereby enabling the other surgical staff members to follow the indicating point indicated by the first assistant 4.

Thus, the endoscopic surgical system according to the present embodiment having such a configuration has advantages as follows. That is to say, the surgical assistant or the like can use the endoscope unit 82 according to the present embodiment as the indicating-point forming means, as well as using the endoscope unit 82 as a device for observing tissue in the body cavity. Thus, the first assistant 4 or the like who operates the endoscope unit 82 can indicate a desired position on tissue in the body cavity using a laser beam emitted from the laser optical fiber probe 85 of the endoscope unit 82.

Note that the operator of the endoscope unit 82 is not restricted to the first assistant 4. For example the surgeon 3 may operate the endoscope unit 82 with the left hand so as to indicate a desired position for other surgical staff members.

Next, description will be made regarding a sixth embodiment according to the present invention with reference to FIG. 10. The endoscopic surgical system according to the present embodiment has a configuration modified based upon that of the first embodiment (see FIGS. 1 through 3) as follows.

That is to say, the endoscopic surgical system according to the present embodiment has a configuration wherein the first and second assistants 4 and 5 may operate two endoscopes at the same time, modified based upon the configuration of the first embodiment wherein only the first assistant 4 operates a single endoscope. Note that the same components as with the first embodiment are denoted by the same reference numerals, and description thereof will be omitted. Note that the endoscope 9, the CCD camera unit 9a, the illumination light transmission cable 17, the electric cable 18, the illumination light source 15, and the camera control unit 14, according to the first embodiment is replaced by a first endoscope 9, a first CCD camera unit 9a, a first illumination light transmission cable 17, a first electric cable 18, a first illumination light source 15, and a first camera control unit 14, respectively, in order to distinguish the aforementioned components from new similar components in the present embodiment.

Figure 10:
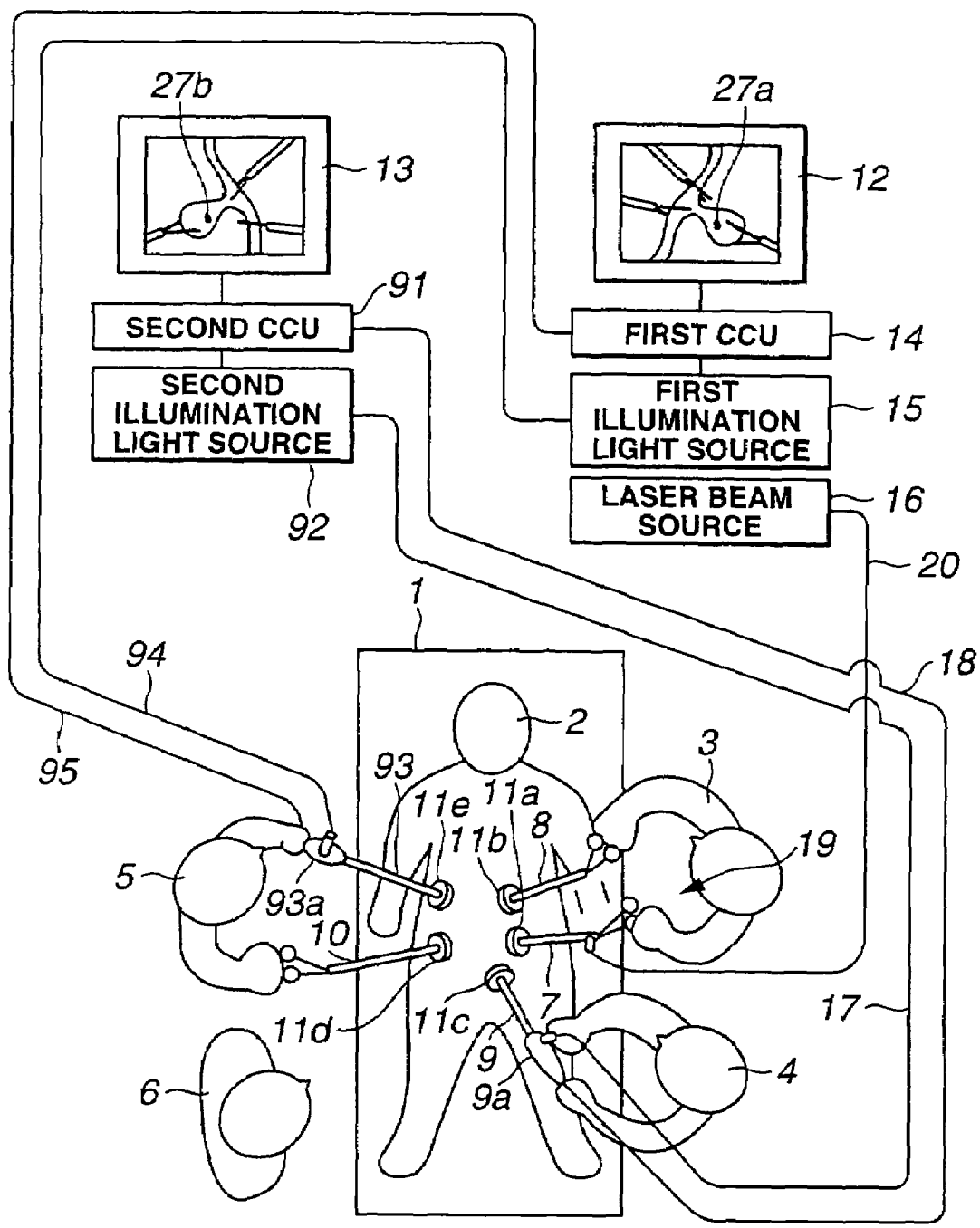
FIG. 10 is a schematic diagram for describing an overall configuration of a surgical system according to a sixth embodiment of the present invention.

With an arrangement according to the present embodiment, the surgeon 3 and the first assistant 4 take up positions on the right side of the surgery table 1 in FIG. 10, as well as the second assistant 5 and the nurse 6 taking up positions on the left side thereof in the drawing. Furthermore, the first monitor 12 is installed on the right side of the surgery table 1, and the second monitor 13 is installed on the left side thereof. In this case, the surgeon 3 and the first assistant 4 on the right side of the surgery table perform monitoring through the screen of the second monitor 13 installed on the left side of the surgery table 1 in many situations, as well as the second assistant 5 and the nurse 6 on the left side of the surgery table 1 performing monitoring through the screen of the first monitor 12 on the right side of the surgery table 1 in many situations.

Furthermore, a second camera control unit (second CCD) 91 and a second illumination light source 92 are installed near the second monitor 13. In this case, the first illumination light transmission cable 17 connected to the first endoscope 9 serving as an observation device which is to be operated by the first assistant 4 is connected to the second illumination light source 92.

Furthermore, the first CCD camera unit 9a mounted on the rear end of the first endoscope 9 is connected to the second camera control unit 91 through the first electric cable 18. Furthermore, the second camera control unit 91 is connected to the second monitor 19. Accordingly, an endoscopic image taken by the first endoscope 9 is displayed on the second monitor 13. Note that the surgeon 3 and the first assistant 4 perform surgery while monitoring the endoscopic images displayed on the second monitor 13 in many situations.

On the other hand, the second assistant 5 operates a second endoscope 93 serving as an observation device in one hand. The insertion portion of the second endoscope 93 is inserted into the insertion hole of the tube of a trocar 11e which has been inserted through the abdominal wall of the patient 2 beforehand, whereby the insertion portion of the second endoscope 93 is inserted into the body of the patient 2 through the insertion hole of the trocar 11e.

A second illumination light cable 94 connected to the second endoscope 93 is connected to the first illumination light source 15. Furthermore, a second CCD camera unit 93a mounted on the rear end of the second endoscope 93 is connected to the first camera control unit 14 through a second electric cable 95.

The first camera control unit 14 is connected to the first monitor 12. Accordingly, an endoscopic image of the portion subjected to surgery, which has been taken by the second endoscope 93, is displayed on the first monitor 12. Note that the second assistant 5 and the nurse 6 perform surgery while monitoring the endoscopic images displayed on the first monitor 12 in many situations.

Note that all the surgical staff members can perform monitoring through either of the first and second monitors 12 and 13, and thus, all the surgical staff members can perform surgery while performing monitoring through a suitable monitor as necessary.

In this case, a position formed of a laser beam spot emitted from the tip of the laser forceps 19 operated by the surgeon 3 is displayed as the indicating point 27 on the first monitor 12 and the second monitor 13.

Next, description will be made regarding operations of the present embodiment having such a configuration. At the time of use of the endoscopic surgical system according to the present embodiment, the surgeon 3 can indicate a desired position on tissue in the body cavity as the indicating point 27 using a laser beam emitted from the laser forceps 19 operated by the surgeon 3.

The indicating point 27 indicated by the surgeon 3 is observed through the first endoscope 9 and the second endoscope 93. Observation images taken by the first endoscope 9 are displayed on the second monitor 13, and on the other hand, observation images taken by the second endoscope 93 are displayed on the first monitor 12. This allows the surgical staff members such as the first and second assistants 4 and 5, the nurse 6, and so forth, to monitor surgery through the monitors 12 and 13.

Furthermore, with the present embodiment, the first and second assistants 4 and 5 operate the endoscopes 9 and 93, respectively. Thus, the first and second assistants 4 and 5 can each perform surgical treatment while monitoring images taken by his/her own endoscope.

Thus, the endoscopic surgical system according to the present embodiment having such a configuration has advantages as follows. That is to say, with the present embodiment, the surgeon 3 can use the laser forceps 19 as a forceps for medical treatment, as well as allowing the surgeon 3 to indicate a desired position on tissue in the body cavity as the indicating point 27 using a laser beam emitted from the laser forceps 19 operated by the surgeon 3 in the same way as with the first embodiment. The surgical staff members such as the first and second assistants 4 and 5, the nurse 6, and so forth, can confirm the positions of the indicating points 27a and 27b on the first and second monitors 12 and 13, thereby enabling the surgical staff members to follow the precise position of the indicating point 27 indicated by the surgeon 3. Thus, the surgeon 3 can use the laser forceps 19 as indicating-point forming means for forming the indicating point 27 at a desired position on tissue in the body cavity for other surgical staff members. Thus, in a case of multiple surgical staff members performing surgery under endoscopic observation, the endoscopic surgical system according to the present embodiment facilitates communication between the surgeon 3 and the other surgical staff members, thereby enabling smooth surgery, and thereby reducing the load of the surgical staff members, as well as reducing surgery time.

Furthermore, the endoscopic surgical system according to the present embodiment further has advantages as follows, in addition to the aforementioned same advantages as with the first embodiment. That is to say, with the present embodiment, the surgeon 3 and the first assistant 4 on the right side of the surgery table 1 perform monitoring through the screen of the second monitor 13 on the left side of the surgery table 1 in many situations, and on the other hand, the second assistant 5 and the purse 6 on the left side of the surgery table 1 perform monitoring through the screen of the first monitor 12 on the right side of the surgery table 1 in many situations. Accordingly, the surgeon 3 and the second assistant 5 perform monitoring through different images in many situations, leading to difficulty in performing surgery while performing monitoring in cooperation with each other.

The endoscopic surgical system according to the present embodiment allows the surgeon 3 and the second assistant 5 to monitor a single indicating point formed on tissue in the body cavity as the indicating point 27 through the first and second monitors 12 and 13, respectively. Thus, this endoscopic surgical system allows the surgeon 3 and the second assistant 5 to perform surgery in cooperation with each other, regardless of the fact that the surgeon 3 and the second assistant 5 perform monitoring with different images.

Figure 11:
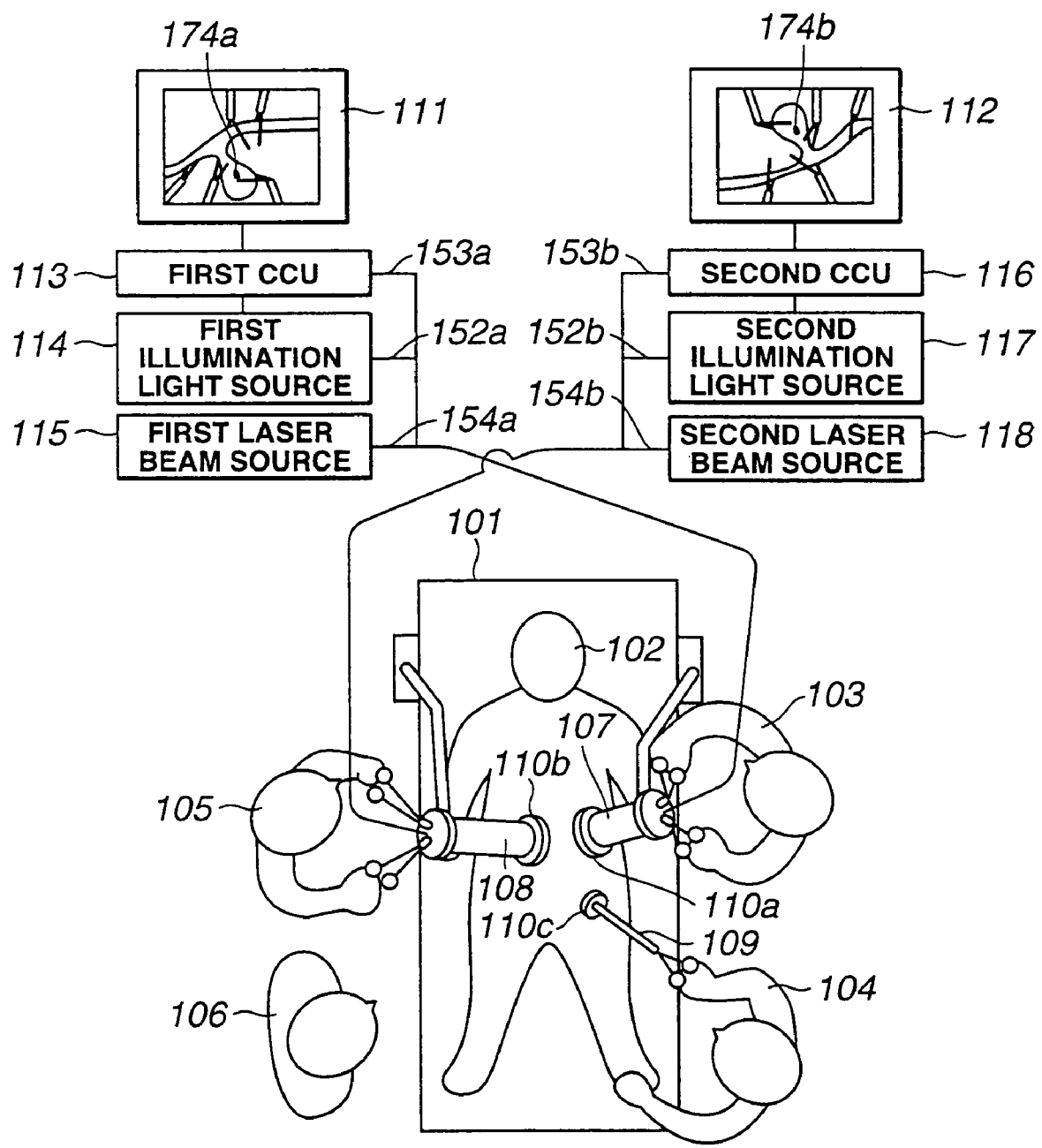
FIGS. 11 through 30 are diagrams for describing a seventh embodiment according to the present invention.

Next, description will be made regarding a seventh embodiment according to the present invention with reference to FIGS. 11 through 30. FIG. 11 is a diagram for describing surgery using an endoscopic surgical system according to the present embodiment. In FIG. 11, reference numeral 101 denotes a surgery table. A patient 102 lies on the surgery table 101. Multiple surgical staff members such as a surgeon 103, a first assistant 104, a second assistant 105, a nurse 106, and the like, take up positions around the surgery table 101 so as to perform surgical treatment in cooperation with each other. In this case, the surgeon 103 and the first assistant 104 take up positions on the right side of the surgery table 101 in FIG. 11, and on the other hand, the second assistant 105 and the nurse 106 take up positions on the left side of the surgery table 101 in the drawing.

The surgeon 103 holds a first surgical instrument 107 in both hands so as to perform surgery. In the same way, the second assistant 105 holds a second surgical instrument 108 in both hands so as to perform surgery. On the other hand, the first assistant 104 holds a surgical instrument such as the forceps 109, for example, so as to assist the surgeon 103 and the second assistant 105.

Furthermore, a predetermined number of (three, in the present embodiment) trocars 110*a* through 110*c* are inserted through the abdominal wall of the patient 102 beforehand, corresponding to the number of the first surgical instrument 107, the second surgical instrument 108, and the forceps 109, which are to be used at the same time. Then, the first surgical instrument 107, the second surgical instrument 108, and the forceps 109, are inserted through the trocars 110*a* through 110*c*, respectively, whereby these surgical instruments are inserted into the body of the patient 102 through the trocars 110*a* through 110*c*.

Furthermore, two monitors serving as image display means, specifically, a first monitor 111 and a second monitor 112 are installed near the surgery table 101 in the surgery room. In this case, the first monitor 111 is installed on the left side of the surgery table 101, and the second monitor 112 is installed on the right side of the surgery table 101.

Furthermore, a first camera control unit (first CCU) 113, a first illumination light source 114, and a first laser beam source 115, are installed near the first monitor 111. In the same way, a second camera control unit (second CCU) 116, a second illumination light source 117, and a second laser beam source 118, are installed near the second monitor 112.

Next, description will be made regarding the first surgical instrument 107 and the second surgical instrument 108. Note that the first surgical instrument 107 and the second surgical instrument 108 have the same configuration, and accordingly, description will be made below regarding the first surgical instrument 107, and description of the second instrument 108 will be omitted.

Figure 12:
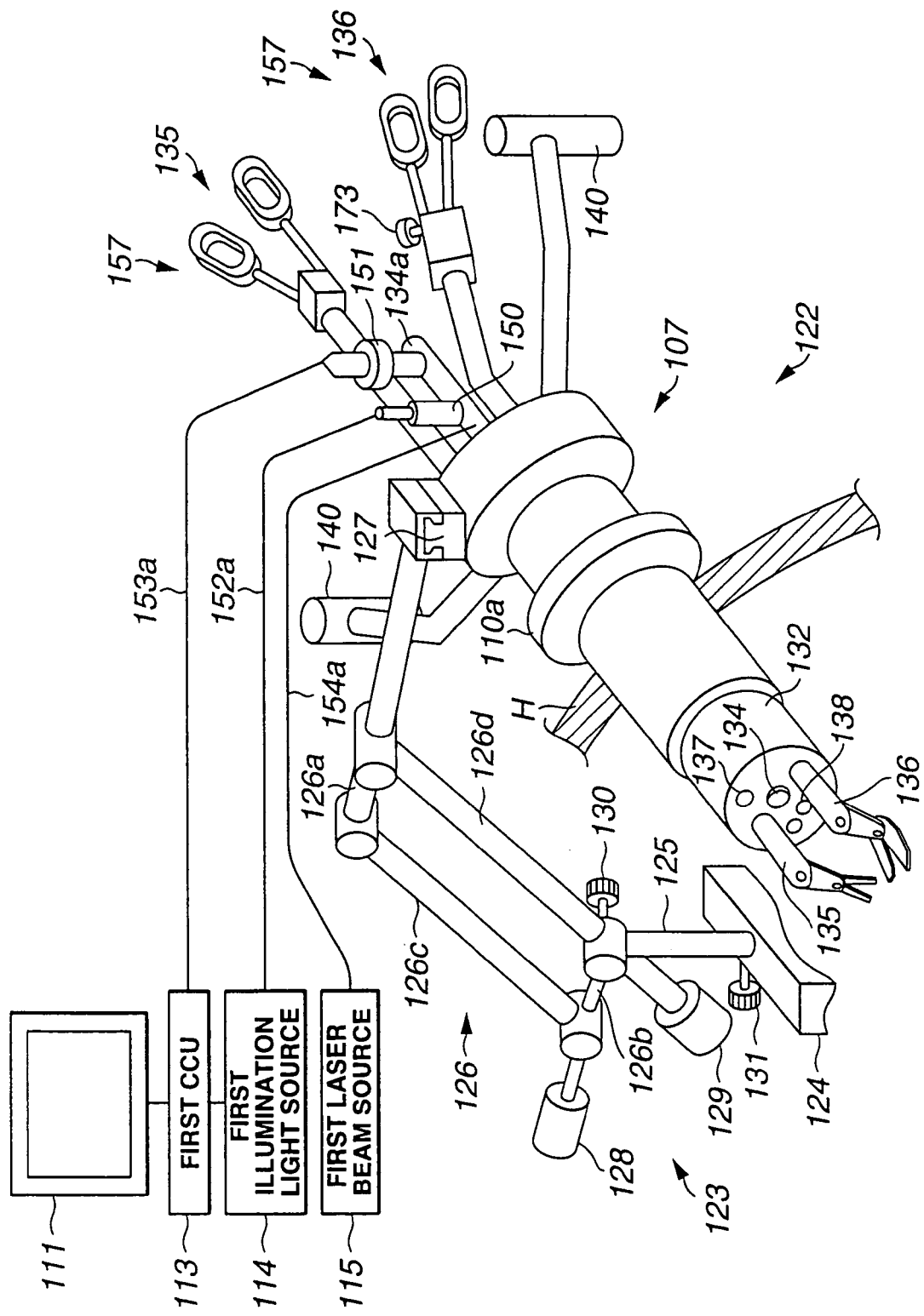

FIG. 12 is a schematic diagram which shows a configuration of the entire endoscopic surgical system according to the present embodiment employing the first surgical instrument 107. The surgical instrument 107 comprises an operation unit 122 serving as an instrument unit, and a support device 123 for supporting the operation unit 122. In this case, the support device 123 includes a base 124 for being fixed to a fixed portion such as the surgery table, the floor of the surgery room, or the like. Furthermore, the support device 123 includes a support shaft 125 erected on the base 124 in a direction generally orthogonal thereto. Note that the support shaft 125 is turnably supported by the base 124.

Furthermore, the support device 123 includes a link mechanism unit 126 formed generally in the shape of a parallelogram mounted on the upper end of the support shaft 125. The link mechanism unit 126 is formed of a pair of horizontal link arms 126*a* and 126*b*, parallel one to another, and a pair of altitude link arms 126*c* and 126*d*, parallel one to another. Furthermore, the horizontal link arm 126*a* serving as the upper side of the parallelogram includes the tip extending therefrom in the horizontal direction, and a mounting member 127 is disposed at the extending tip for mounting the operation unit 122.

Furthermore, the horizontal link arm 126*b* serving as the lower side of the parallelogram, which is the shape of the link mechanism unit 126, includes a first balancer weight 128 on the rear end thereof. Furthermore, the altitude link arm 126*d* serving as the altitude side of the parallelogram includes a second balancer weight 129 at the lower end thereof. Note that the weight and position of the first balancer weight 128 and the second balancer weight 129 are determined so as to keep the balance with the operation unit 122 mounted to the mounting member 127.

Furthermore, a first adjustment knob 130 is disposed at the joint between the altitude link arm 126*d* and the horizontal link arm 126*b* crossing each other. Furthermore, the base 124 includes a second adjustment knob 131 for adjusting motion of the support shaft 125. The surgeon can adjust the degree of ease of operationality of the link mechanism unit 126, i.e., the load for operating the link mechanism unit 126, by adjusting the tightness of the first adjustment knob 130 and the second adjustment knob 131.

Figure 13:
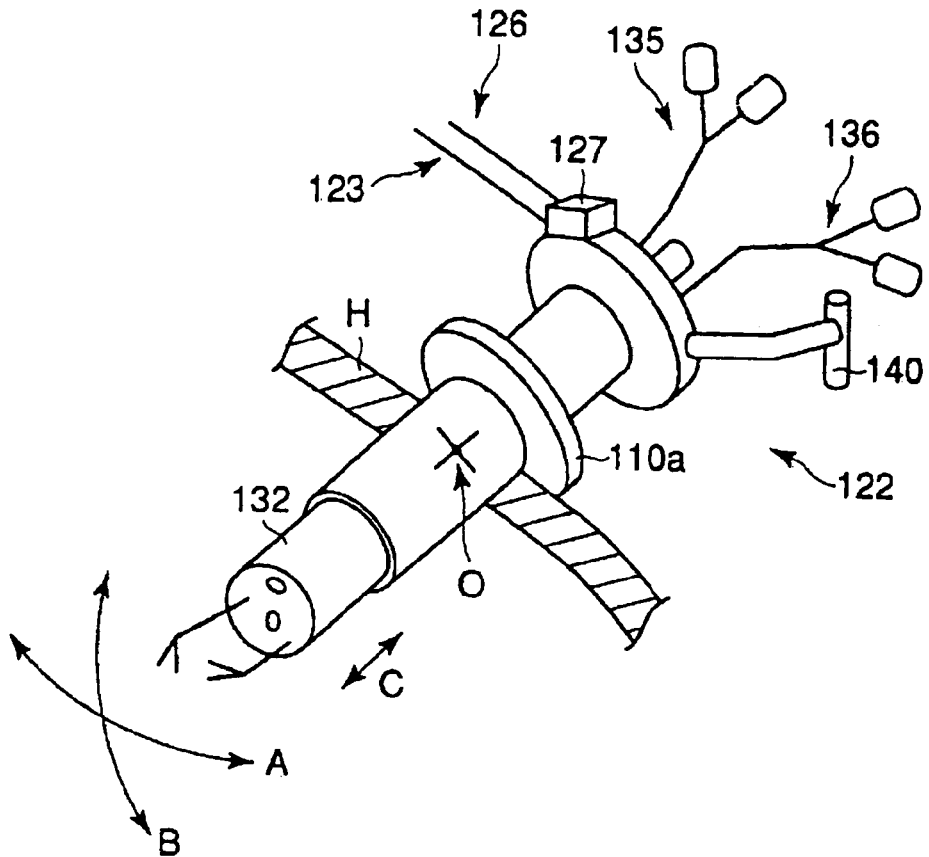

On the other hand, the operation unit 122 includes an insertion portion 132 formed in the shape of a shaft for being inserted into the body of the patient. As shown in FIG. 13, the insertion portion 132 is inserted into the trocar 110*a*, which has been inserted through a body wall H such as abdominal wall or the like of the patient beforehand, whereby the insertion portion 132 is inserted into the body of the patient through the trocar 110*a*.

The insertion portion 132 is supported by the support device 123. Furthermore, as shown in FIG. 13, the link mechanism unit 126 of the support device 123 allows the insertion portion 132 to be turned in a first turning direction denoted by arrow A in FIG. 13, and a second turning direction denoted by arrow B in the drawing, with the insertion point O on the body wall H of the patient 102, through which the trocar 110*a* has been inserted, as the center. Furthermore, the insertion portion 132 has a mechanism so as to be moved in the axial direction along the trocar 110*a* as denoted by arrow C shown in FIG. 13.

Figure 14:
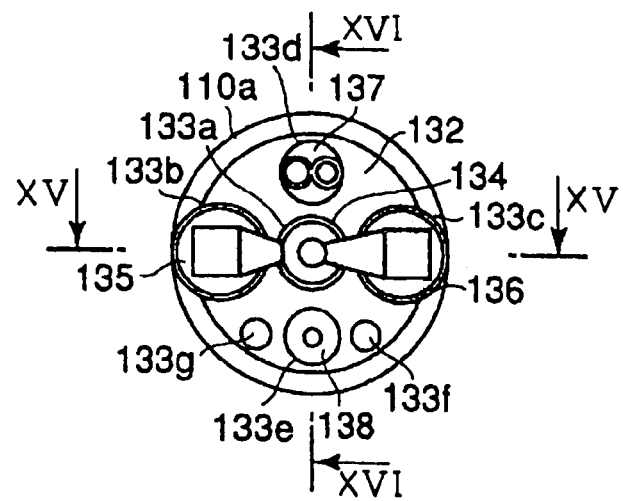
Figure 15:
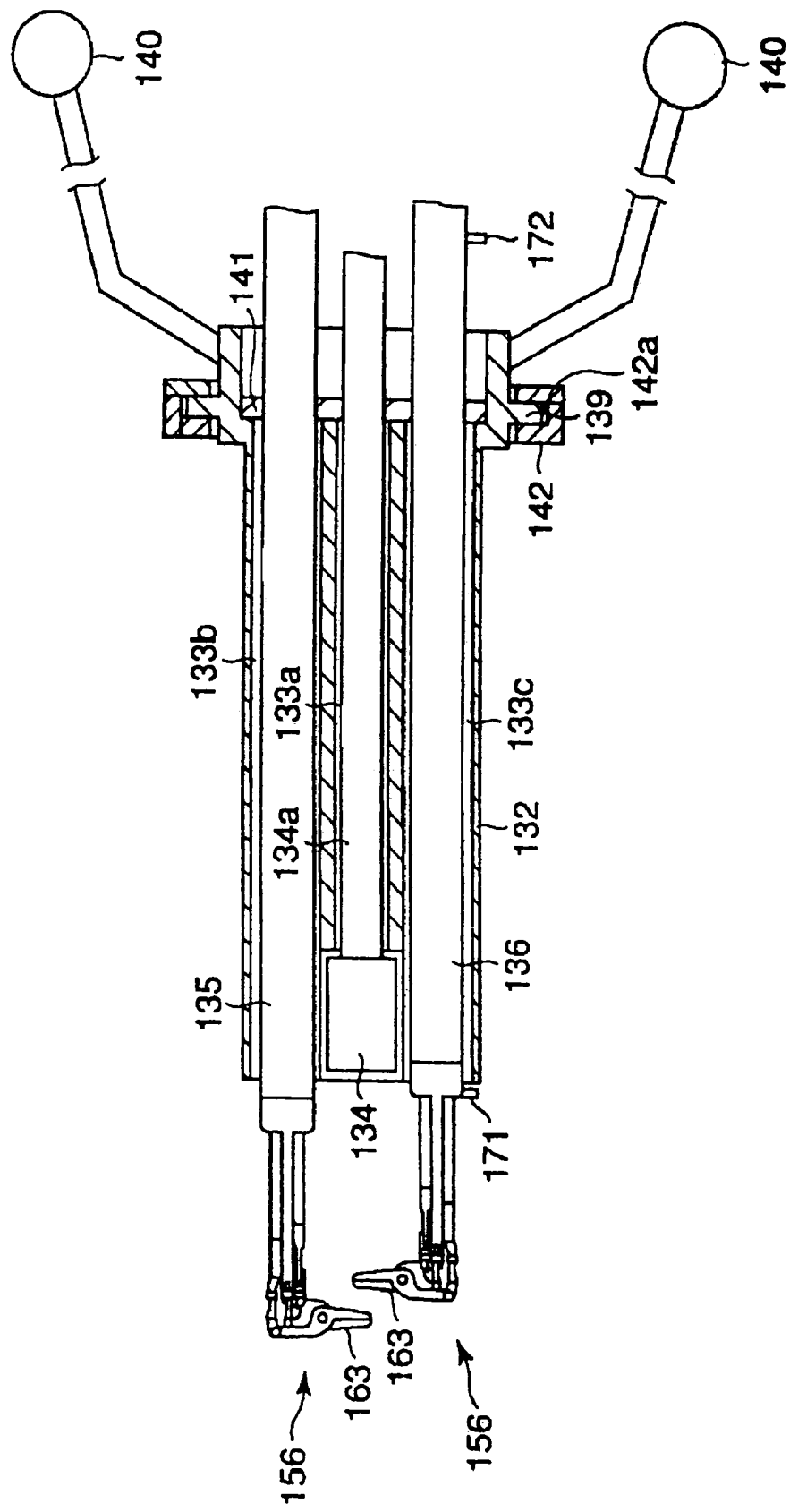
Figure 16:
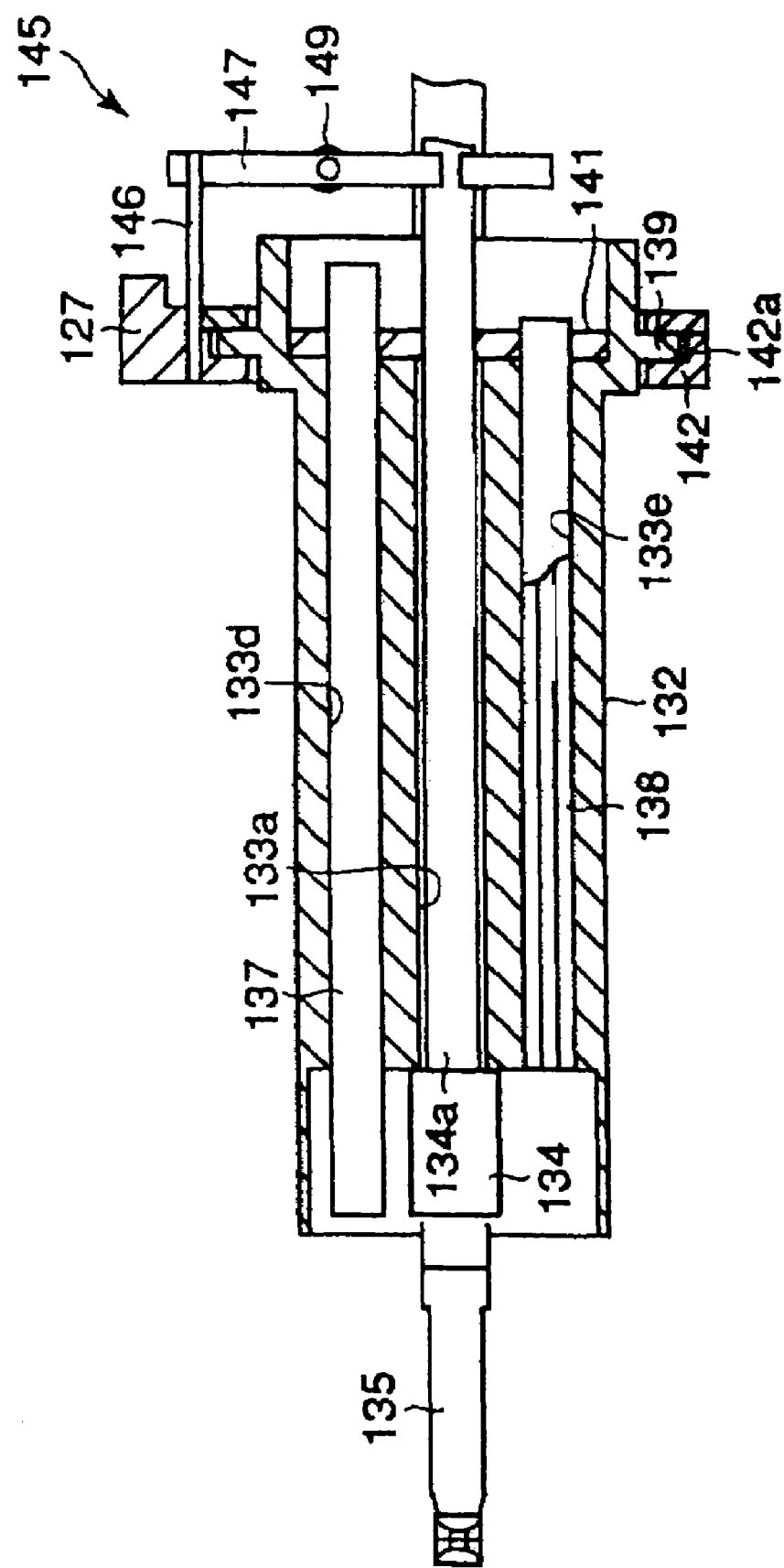

FIG. 14 is a diagram which shows the tip face of the insertion portion 132, FIG. 15 is a cross-sectional view taken along line XV-XV in FIG. 14, and FIG. 16 is a cross-sectional view taken along line XVI-XVI in FIG. 14. As shown in FIGS. 14 through 17, the insertion portion 132 includes multiple (seven, in the present embodiment) channels 133*a* through 133*g*, formed generally parallel one to another along the axial direction thereof. That is to say, the insertion portion 132 is formed of a multi-lumen tube (7-lumen tube, in the present embodiment).

In this case, the channel 133*a* formed at an axial position of the insertion portion 132 includes a camera support shaft 134a inserted thereinto for supporting a CCD camera 134 serving as observing means. That is to say, the channel 133a serves as a camera guide opening.

Furthermore, as shown in FIG. 14, the insertion portion 132 includes channels 133b and 133c formed on both sides of the channel 133a formed at the axial position, for inserting first and second joint forceps 135 and 136, respectively, serving as surgical instruments described later. That is to say, the channel 133b serves as a forceps guide opening for the first forceps 135, and the channel 133c serves as a forceps guide opening for the second forceps 136.

None of the forceps guide openings allow movement of the forceps except for movement along the axial direction thereof, and rotation on the axis thereof, and accordingly, movement other than the movement along the axial direction and rotation around the axis is conveyed as the entire movement of that insertion portion 132. That is to say, upon the surgeon moving the forceps in a direction other than the movement along the axial direction and rotation on the axis, the forceps guide opening conveys the movement to the insertion portion 132, whereby the insertion portion 132 is moved corresponding to the movement. Thus, the operation unit 122 is a multi-function instrument integrally formed of forceps serving as a surgical instrument and an observation device.

On the other hand, as shown in FIG. 14, the channel 133d formed on the upper side of the channel 133a at the axial position includes a light guide 137 formed of an optical fiber, which is inserted therethrough for guiding light. Furthermore, as shown in FIG. 14, the channel 133e formed on the lower side of the channel 133a at the axial position includes a laser optical fiber probe 138 serving as a laser probe, which is inserted therethrough. Furthermore, the insertion portion 132 includes the channels 133f and 133g formed on both sides of the channel 133e serving as surgical-instrument insertion openings for inserting other surgical instruments.

Furthermore, as shown in FIG. 15, the insertion portion 132 includes a flange portion 139 on the outer face of the base end thereof for being mounted onto the support device 123. Furthermore, the insertion portion 132 includes a pair of handles 140 on the base end of thereof. Note that the insertion portion 132 includes a seal member 141 on the inner face of the base end thereof.

On the other hand, the mounting member 127 of the support device 123 includes a flange bearing 142. The flange bearing 142 includes a flange insertion groove 142a on the inner face thereof. As shown in FIGS. 15 and 16, the flange portion 139 of the insertion portion 132 is inserted into the flange insertion groove 142a. Thus, the insertion portion 132 is supported so as to be capable of turning in the axial direction thereof along the flange insertion groove 142a of the flange bearing 142 formed on the mounting member 127 of the support device 123.

Figure 17:
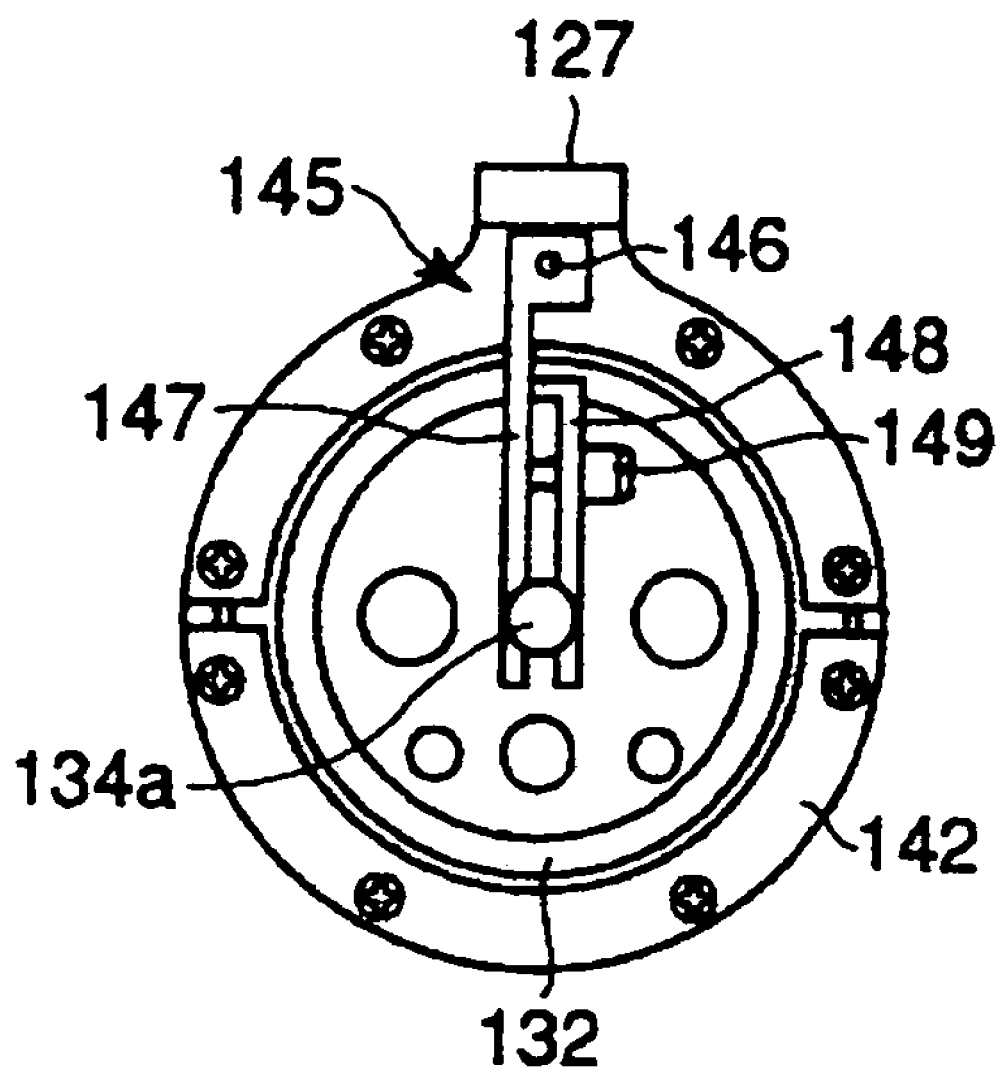

Furthermore, as shown in FIG. 17, the mounting member 127 of the support device 123 is fixed on the outer face of the flange bearing 142. The flange bearing 142 includes a scope support base 145 on the outer face of the rear end as shown in FIG. 17. The scope support base 145 includes a scope support arm 146 on the outer face of the rear end of the flange bearing 142 so as to protrude therefrom.

As shown in FIG. 16, the tip of the scope support arm 146 is connected to one end of a first scope support member 147. Furthermore, a second scope support member 148 formed generally in the shape of a "L" is disposed so as to face the other end of the first scope support member 147 as shown in FIG. 17. With such a configuration, the camera support shaft 134a is supported between the first scope support member 147 and the second scope support member 148. Note that a scope fixing screw 149 is provided between the first scope support member 147 and the second scope support member 148. This keeps the camera support shaft 134a fixed even if the insertion portion 132 is turned in the axial direction thereof along the flange insertion groove 142a of the flange bearing 142 formed on the mounting member 127 of the support device 123.

Furthermore, as shown in FIG. 12, the base end of the camera support shaft 134a includes an optical cable connector 150 and an electric connector 151. The optical cable connector 150 is connected to one end of an illumination light transmission cable 152a, wherein the other end thereof is connected to the first illumination light source 114. On the other hand, the electric connector 151 is connected to one end of a first electric cable 153a, wherein the other end thereof is connected to the first camera control unit 113. The first camera control unit 113 is connected to the first monitor 111. With such a configuration, observation images taken by the CCD camera 134 are displayed on the monitor 111.

Furthermore, one end of a first laser transmission cable 154a is connected to the base end of the camera support shaft 134a. On the other hand, the other end of the first laser transmission cable 154a is connected to the first laser beam source 115. Note that the base end of the laser optical fiber probe 138 is connected to the connection portion between the camera support shaft 134a and the first laser transmission cable 154a. With the aforementioned configuration, a laser beam transmitted through the first laser transmission cable 154a is emitted from the tip of the insertion portion 132 of the operation unit 122.

Next, description will be made regarding a configuration of the first forceps 135 serving as the first surgical instrument 107 of the endoscopic surgical system according to the present embodiment with reference to FIGS. 18 through 22. Note that the first and second forceps 135 and 136 have generally the same configuration. Accordingly, description will be made below regarding the configuration of the first forceps 135 only. Note that the same components of the second forceps 136 as with the first forceps 135 are denoted by the same reference numerals, and description thereof will be omitted.

Figure 18:
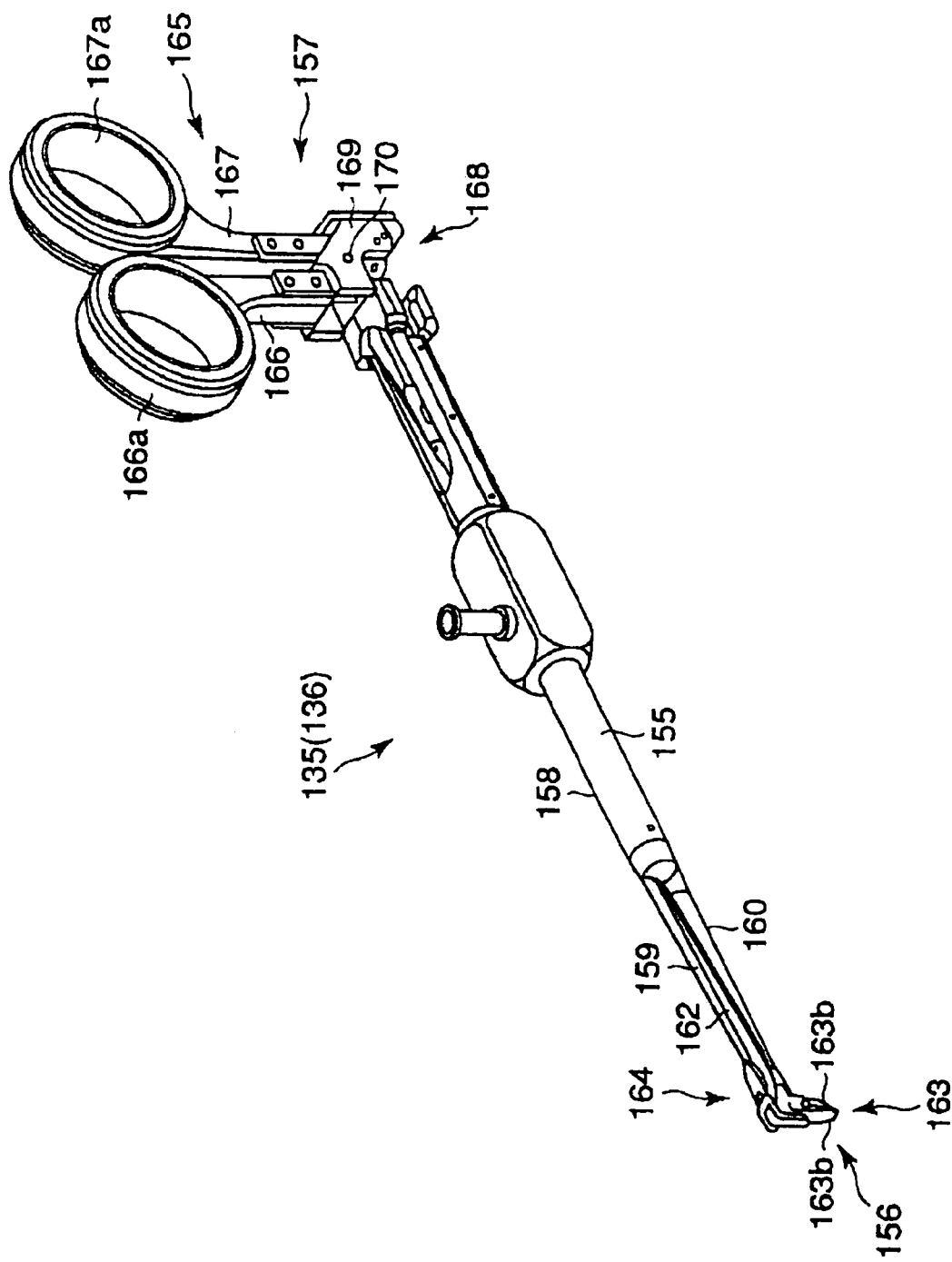

FIG. 18 is an overall external view of the first forceps 135 according to the present embodiment. That is to say, the first forceps 135 according to the present embodiment comprises a long and narrow insertion portion 155 formed generally in the shape of a shaft, a manipulator-hand portion 156 disposed on the tip of the insertion portion 155, and an operation portion 157 disposed on the base end of the insertion portion 155. Note that the first forceps 135 comprise multi-joint forceps having a function wherein the manipulator-hand portion 156 can be turned in the direction displaced from the axial direction of the insertion portion 155 as disclosed in Japanese Unexamined Patent Application Publication No. 2001-299768, for example.

The insertion portion 155 includes a sheath 158 formed of a long and small-diameter tube in the shape of a straight tube. The sheath 158 includes three driving rods, i.e., a first driving rod 159, a second driving rod 160, and a third driving rod 161, therewithin, generally parallel one to another. In this case, the first driving rod 159 forms an open/close link formed of a small-diameter rod. On the other hand, the second driving rod 160 and the third driving rod 161 form a rotational link.

Figure 19:
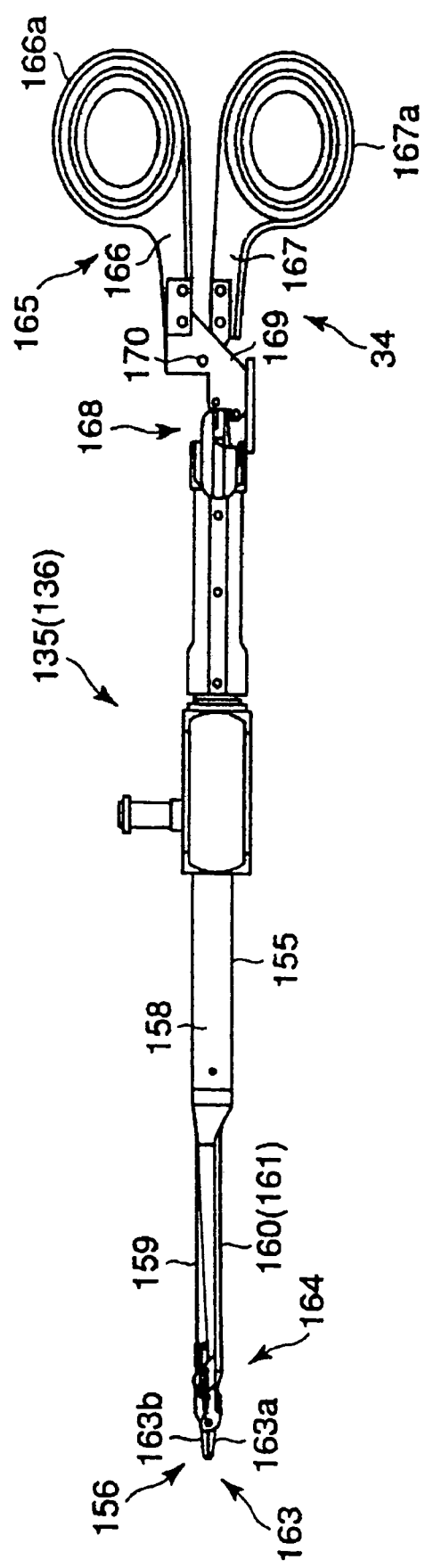
Figure 21:
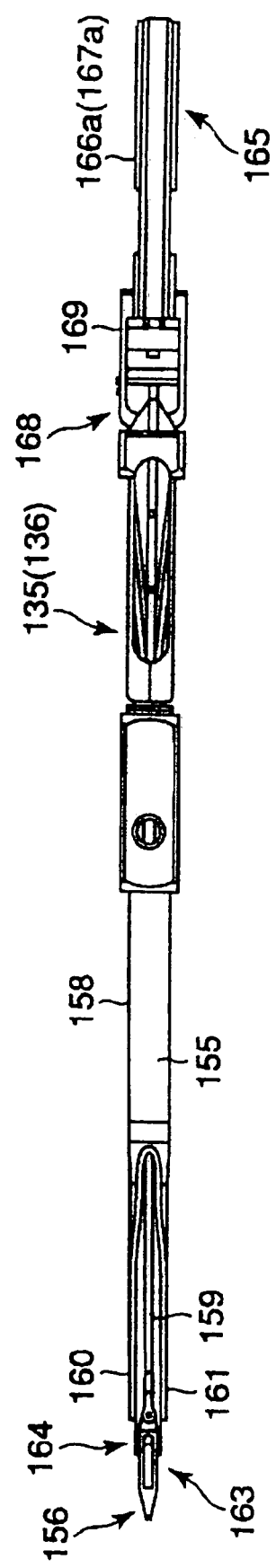

Note that the first driving rod 159 is disposed on the upper side of the axis of the insertion portion 155 as shown in FIG. 19. On the other hand, the second and third driving rods 160 and 161 are disposed on the lower side of the axis of the insertion portion 155. Furthermore, the second and third driving rods 160 and 161 are disposed horizontally symmetrically as shown in FIG. 21, and are supported so as to be capable of sliding in the axial direction independently of each other.

On the other hand, the manipulator-hand portion 156 has a configuration as follows. That is to say, the insertion portion 155 includes the tip protruding forward therefrom, and a rigid support portion 162 integrally formed on the tip. The tip of the support portion 162 includes a jaw 163 and a tip link mechanism 164. The jaw 163 includes a pair of manipulator-hand members 163a and 163b so as to be capable of opening and closing. The tip link mechanism 164 is connected to the tips of the first, second, and third driving rods 159, 160, and 161, as well as being connected to the base end portion of the manipulator-hand members 163a and 163b. The tip link mechanism 164 allow the surgeon to perform open/close control of the jaw 163 between the manipulator-hand members 163a and 163b by sliding actions of the first driving rod 159. Furthermore, this mechanism 164 allows the surgeon to control the entire jaw 163 so as to turn to deviate from an axis of the insertion portion 155 by actions of the second and third driving rods 160 and 161.

On the other hand, the operation portion 157 includes a handle unit 165 for operating the manipulator-hand portion 156. The handle unit 165 comprises a pair of forceps handles, i.e., a first handle 166 and a second handle 167, and an operation-portion link mechanism 168.

Furthermore, the handle unit 165 includes a handle support portion 169. The handle support portion 169 includes a shaft 170 for turnably connecting the pair of handles 166 and 167 with one ends thereof. On the other hand, the other end of the first handle 166 includes a finger ring 166a for the surgeon to place a finger other than the thumb, and the other end of the second handle 167 includes a finger ring 167a for the surgeon to place the thumb.

Furthermore, the operation-portion link mechanism 168 is connected to the base ends of the first, second, and third driving rods 159, 160, and 161, as well as being connected to the one ends of the pair of handles 166 and 167. Note that the operation-portion link mechanism 168 is connected to the pair of handles 166 and 167 so as to allow the surgeon to perform open/close actions between the handles 166 and 167, and to turn the entire handle unit 165 so as to be deviated from the axial direction of the insertion portion 155.

That is to say, in operations of the first forceps 135, upon the surgeon performing open/close actions between the pair of handles 166 and 167 with the shaft 170 as an axis, the first driving rod 159 is moved along the axial direction thereof. In this case, upon the surgeon opening the pair of handles 166 and 167, the first driving rod 159 is moved forward, and the jaw 163 formed of the first and second manipulator-hand members 163a and 163b is opened.

On the other hand, upon the surgeon closing the pair of handles 166 and 167, the first driving rod 159 is moved backward, and the jaw 163 formed of the first and second manipulator-hand members 163a and 163b is closed. Thus, the surgeon can perform open/close control of the jaw 163 between the pair of manipulator-hand members 163a and 163b by operating the first and second handles 166 and 167.

Figure 20:
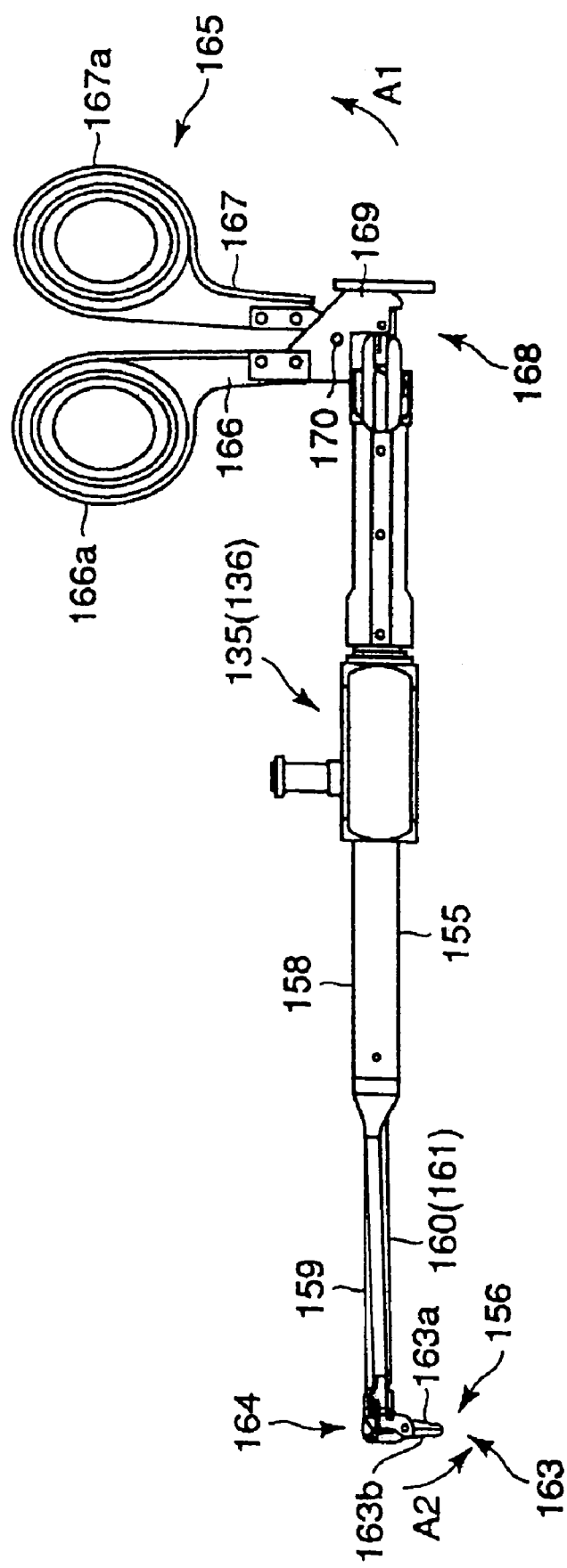

The first forceps 135 with the handle unit 165 according to the present embodiment has a configuration wherein the handle unit 165 can be turned on two axes (first axis in FIG. 20, and second axis in FIG. 22) so as to be displaced from the axial direction of the insertion portion 155 from the normal state wherein the insertion portion 155 and the handle unit 165 form a straight line as shown in FIGS. 19 and 20 (FIG. 19 is a side view thereof, and FIG. 21 is a top view thereof).

FIG. 19 shows the first forceps 135 with the handle unit 165 according to the present embodiment in the normal state wherein the insertion portion 155 and the handle unit 165 form a straight line as viewed from the side wherein the pair of handles 166 and 167 are opened and closed. In this case, at the time of the first forceps 135 with the handle unit 165 being in the normal state shown in FIG. 19, the jaw 163 of the manipulator-hand portion 156 is kept straight along the axial direction of the insertion portion 155.

On the other hand, FIG. 20 shows the first forceps 135 with the handle unit 165 turned counterclockwise as shown by arrow A1 in FIG. 20, i.e., in a first turning direction, from the normal state shown in FIG. 19. In this case, the handle unit 165 is turned in the direction of the first handle 166, generally orthogonal to the axial direction of the insertion portion 155. Upon the surgeon turning the handle unit 165 as shown in FIG. 20, the jaw 163 of the manipulator-hand portion 156 is turned in the same direction as with the handle unit 165 (in the counterclockwise direction in FIG. 20) as shown by arrow A2 in FIG. 20, generally orthogonal to the axial direction of the insertion portion 155. Thus, the surgeon can control the jaw 163 of the manipulator-hand portion 156 so as to turn around the first axis, i.e., in the first turning direction so as to be displaced from the axial direction of the insertion portion 155.

On the other hand, FIG. 21 is a view which shows the first forceps 135 with the handle unit 165 in the normal state shown in FIG. 19, as viewed from the side turned by 90° around the axial direction of the insertion portion 155. In this case, at the time of the first forceps 135 with the handle unit 165 being kept straight along the axial direction of the insertion portion 155, i.e., being in the normal state shown in FIG. 21, the jaw 163 of the manipulator-hand portion 156 is kept straight along the axial direction of the insertion portion 155.

Figure 22:
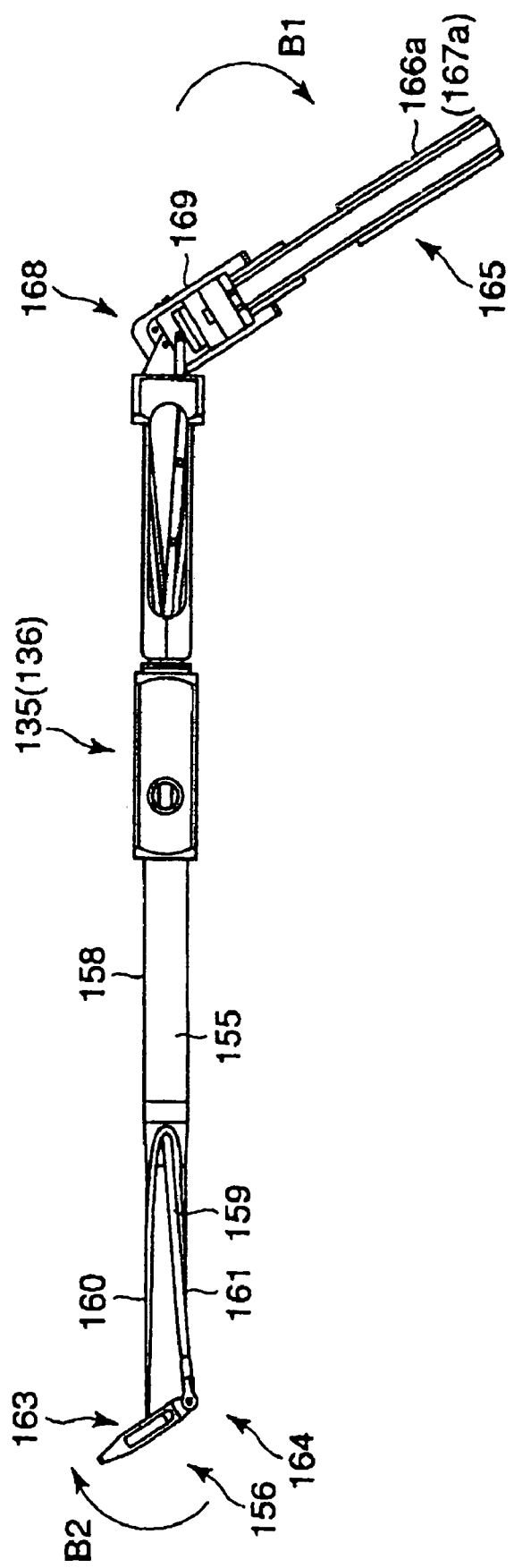

On the other hand, FIG. 22 shows the first forceps 135 with the handle unit 165 turned in the second turning direction, i.e., clockwise as shown by arrow B1 in FIG. 22, from the normal state shown in FIG. 21. At this time, the handle unit 165 is turned so as to be positioned slanting downward from the axial direction of the insertion portion 155 as shown in FIG. 22. Upon the surgeon turning the handle unit 165 as shown in FIG. 22, the jaw 163 of the manipulator-hand portion 156 is turned in the same turning direction as with the handle unit 165 as shown by arrow B2 in FIG. 22 so as to be displaced from the axial direction of the insertion portion 155, and so as to be positioned slanting upward from the axial direction of the insertion portion 155. Thus, the surgeon can control the jaw 163 of the manipulator-hand portion 156 so as to turn around the second axis, i.e., in the second turning direction (which is different from the first turning direction shown in FIG. 20) so as to be displaced from the axial direction of the insertion portion 155. Thus, the first forceps 135 according to the present embodiment have a configuration wherein the surgeon can control the jaw 163 of the manipulator-hand portion 156 so as to be freely turned around two axes other than the axis of the insertion portion 155 in two turning directions (the first turning direction in FIG. 20, and the second turning direction in FIG. 22) so as to be displaced from the axial direction of the insertion portion 155.

Figure 23:
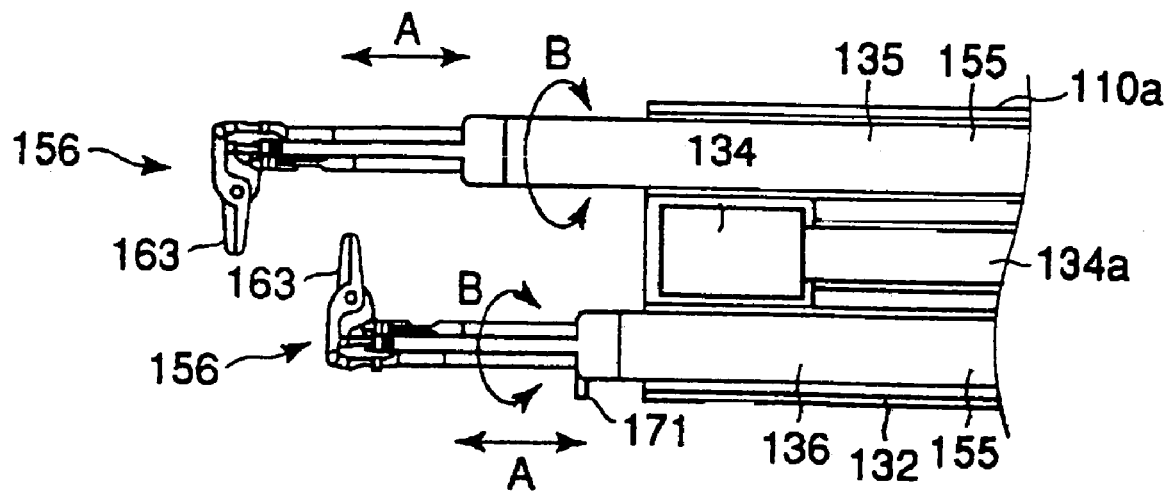

Furthermore, the first forceps 135 and the second forceps 136 are inserted into the channels 133b and 133c serving as forceps guide openings of the insertion portion 132, respectively, and the first forceps 135 and the second forceps 136 are supported by the insertion portion 132 so as to be capable of sliding in the axial direction as to the insertion portion 132 as shown by arrow A in FIG. 23 independently of each other.

As shown in FIG. 15, the insertion portion 155 of the second forceps 136 includes a tip stopper pin 171 serving as a movement limiter protruding on the outer face of the tip thereof. Furthermore, the insertion portion 155 of the second forceps 136 includes a rear-end stopper pin 172 serving as a movement limiter protruding on the outer face of the rear end thereof. In this case, the tip stopper pin 171 and the rear-end stopper pin 172 are formed with a greater interval than the length of the channel 133c serving as a forceps opening formed on the insertion portion 132.

Thus, the second forceps 136 are supported so as to be capable of sliding along the axial direction of the insertion portion 132 between: a tip-limit position where the tip stopper pin 171 comes into contact with the tip face of the insertion portion 132 around the forceps guide opening; and a rear-end limit position where the rear-end stopper pin 172 comes into contact with the rear-end face of the insertion portion 132 around the forceps guide opening.

Furthermore, the first forceps 135 are inserted into the channel 133b of the insertion portion 132 and are supported so as to be capable of rotating around the axis thereof as shown by arrow B in FIG. 23. In the same way, the second forceps 136 are inserted into the channel 133c of the insertion portion 132 and are supported so as to be capable of rotating around the axis thereof. Thus, the first forceps 135 and the second forceps 136 are supported so as to be capable of rotating around the axis thereof independently of each other.

Furthermore, with the endoscopic surgical system according to the present embodiment, as described above, the first surgical instrument 107 includes the light guide 137 and the CCD camera 134 as shown in FIG. 12. The light guide 137 is connected to the first illumination light source 114 through the first illumination light transmission cable 152a. On the other hand, the CCD camera 134 is connected to the first camera control unit 113 through the first electric cable 153a. Thus, the portion subjected to surgery is illuminated with light supplied from the light guide 137, images of this portion are taken by the CCD camera 134, and the surgical staff members can observe the images on the first monitor 111.

Furthermore, the second surgical instrument 108 includes the light guide 137 and the CCD camera 134 in the same way as with the first surgical instrument 107. As shown in FIG. 11, the light guide 137 of the second surgical instrument 108 is connected to the second illumination light source 117 through the second illumination light transmission cable 152b. On the other hand, the CCD camera 134 is connected to the second camera control unit 116 through the second electric cable 153b. Thus, the portion subjected to surgery is illuminated with light supplied from the light guide 137, images of this portion are taken by the CCD camera 134, and the surgical staff members can observe the images on the second monitor 112.

Furthermore, with the endoscopic surgical system according to the present embodiment, each of the first surgical instrument 107 and the second surgical instrument 108 include a laser probe 138 (see FIG. 12). The laser probe 138 included in the first surgical instrument 107 is connected to the first laser beam source 115 through the first laser transmission cable 154a.

Furthermore, as shown in FIG. 12, the second forceps 136 includes a switch 173 near the operation unit 157 thereof for on/off control of laser beam emission, which allows the operator to on/off control of laser beam emission. Upon the operator turning on the switch 173, a laser beam is cast onto tissue in the body cavity from the first surgical instrument 107 so as to form a laser beam spot thereon.

In this case, the laser beam spot on the tissue in the body cavity formed of a laser beam cast from the first surgical instrument 107 operated by the surgeon 103 can be observed as the indicating point 174a on the first monitor 111. In the same way, the laser beam spot formed on the tissue in the body cavity is taken by the CCD camera 134 included in the second surgical instrument 108, whereby the laser beam spot can be observed as the indicating point 174b on the second monitor 112.

With the second surgical instrument 108, the laser probe 138 is connected to the second laser beam source 118 through the second laser transmission cable 154b in the same way as with the first surgical instrument 107.

Furthermore, the second forceps 136 serving as the second surgical instrument 108 include a switch 173 around the operation unit 157 for on/off control of laser emission, which allows the operator to perform on/off control of laser emission. Upon the operator turning on the switch 173, a laser is cast onto tissue in the body cavity from the tip of the second surgical instrument 108 so as to form a laser beam spot thereon.

The laser beam spot thus formed on the tissue in the body cavity by the second assistant 105 with the second surgical instrument 108 can be observed as an indicating point on the first monitor 111 and the second monitor 112 in the same way as with the first surgical instrument 107.

Next, description will be made regarding operations of the endoscopic surgical system according to the present embodiment having the aforementioned configuration. First, at the time of use of the first surgical instrument 107, the operation unit 122 is mounted on the mounting member 127 of the link mechanism unit 126 of the support device 123. The channel 133a serving as a camera guide opening of the insertion portion 132 of the operation unit 122 includes the CCD camera 134 inserted thereinto. Then, the operation unit 122 is inserted into the trocar 110a which has been inserted through the body wall H of the patient beforehand, whereby the operation unit 122 is inserted into the body of the patient through the trocar 110a.

Subsequently, the first forceps 135 is inserted into the channel 133b serving as a forceps guide opening of the insertion portion 132, and the second forceps 136 is inserted into the channel 133c serving as a forceps guide opening. Then, the surgeon 103 can freely move the entire operation unit 122 while holding the first forceps 135 and the second forceps 136 as follows.

The surgeon 103 can move the handle units 165 included in the first and second forceps 135 and 136 vertically and horizontally while holding the handle units 165 so as to turn the operation unit 122 with the insertion point O of the trocar 110a formed on the body wall H of the patient as a center, in the first turning direction as shown by arrow A, and in the second direction orthogonal to the first direction, shown by arrow B, independently of each other, i.e., in any turning direction, as shown in FIG. 13.

On the other hand, as shown in FIG. 15, the surgeon can pull the second forceps 136 such that the tip stopper pin 171 formed so as to protrude on the outer face of the tip end of the insertion portion 155 comes into contact with the tip face of the insertion portion 132 around the forceps guide opening. Upon the surgeon further pulling the second forceps 136 toward the surgeon side in this situation, the insertion portion 132 is moved toward the surgeon side along the axial direction shown by arrow C in FIG. 13.

In the same way, the surgeon can press the second forceps 136 such that the rear-end stopper pin 172 formed so as to protrude on the outer face of the rear end of the insertion portion 155 comes into contact with the rear-end face of the insertion portion 132 around the forceps guide opening. Upon the surgeon further pressing the second forceps 136 forward in this situation, the insertion portion 132 is moved away from the surgeon along the axial direction shown by arrow C in FIG. 13.

Thus, the surgeon can integrally move the operation unit 122 including the CCD camera 134 mounted within the insertion portion 132 thereof, and the first and second forceps 135 and 136, at the same time in the same direction. That is to say, the surgeon can integrally move the CCD camera 134 and the two pairs of forceps 135 and 136. Note that the same movement of the operation unit 122 may be made by the surgeon 103 holding and operating the handles 140 of the first surgical instrument 107.

Thus, the CCD camera 134 serving as observation means and the first and second forceps 135 and 136 can be integrally moved as described above.

Figure 24:
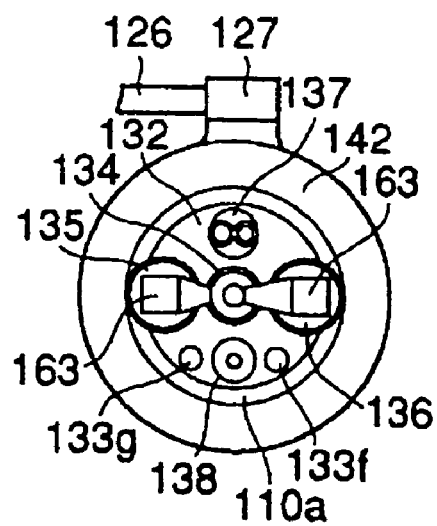

Next, description will be made regarding rotational actions wherein the entire operation unit 122 of the first surgical instrument 107 is turned through the flange bearing 142 of the link mechanism unit 126 of the support device 123 with reference to FIGS. 24 through 26. FIG. 24 is a diagram which shows the operation unit 122 supported through the flange bearing 142 of the link mechanism unit 126 in the normal state, i.e., with a rotation angle of 0. Then, the surgeon can turn the entire operation unit 122 clockwise or counterclockwise by holding and operating the first and second forceps 135 and 136.

Figure 25:
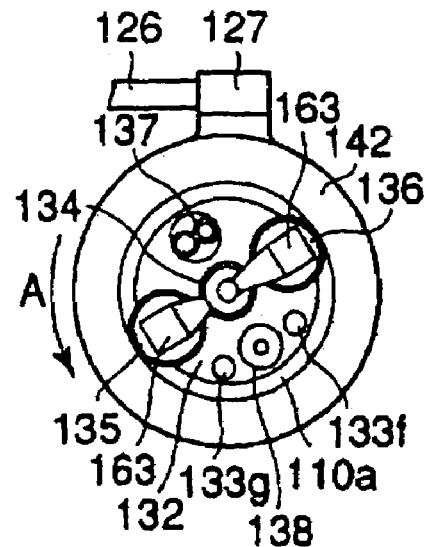
Figure 26:
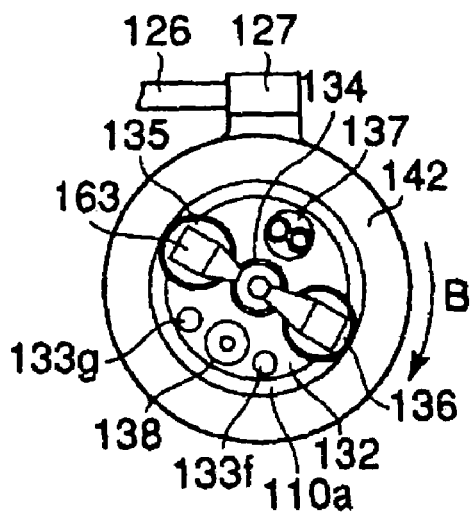

FIG. 25 is a diagram which shows the operation unit 122 which has been turned counterclockwise around the axis thereof from the normal state as shown by arrow A in the drawing. FIG. 26 is a diagram which shows the operation unit 122 which has been turned clockwise around the axis thereof from the normal state as shown by arrow B in the drawing. In this case, the CCD camera 134 of the first surgical instrument 107 is supported by the scope support base 145 while remaining stationary (not turned). Thus, the CCD camera 134 can take images with a stationary field of view regardless of turning of the first and second forceps 135 and 136 at the same time and at the same turning direction due to turning of the operation unit 122. The turning can be made by the surgeon holding and operating the handles 140.

On the other hand, the CCD camera 134 and the first and second forceps 135 and 136 mounted within the insertion portion 132 can be moved independently of each other as follows. That is to say, the surgeon can turn the CCD camera 134 mounted within the channel 133a of the insertion portion 132 around the axis thereof, and can fix the CCD. Furthermore, the surgeon can slide the first forceps 135 and the second forceps 136 along the axial direction thereof as to the insertion portion 132 independently of each other as shown by arrow A in FIG. 23.

Furthermore, the surgeon can turn the first forceps 135 mounted within the channel 133b of the insertion portion 132 around the axis thereof as shown by arrow B in FIG. 23. In the same way, the surgeon can turn the second forceps 136 mounted within the channel 133c of the insertion portion 132 around the axis thereof. Thus, the surgeon can turn the first and second forceps 135 and 136 around the axis thereof independently of each other.

On the other hand, the surgeon can control the first forceps 135 and the second forceps 136 so as to perform open/close actions of each jaw 163 between the pair of manipulator-hand members 163a and 163b by opening/closing the pair of the first and second handle 166 and 167 of the corresponding handle unit 165.

Furthermore, upon the surgeon turning the handle unit 165 of the first forceps 135 in the first turning direction as shown by arrow A1 in FIG. 20 from the normal state wherein the first forceps 135 and the handle unit 165 are kept straight as shown in FIG. 19, the jaw 163 of the manipulator-hand portion 156 is turned in the same direction of the movement of the handle unit 165 as shown by arrow A2 in FIG. 20, generally orthogonal to the axial direction of the insertion portion 155.

On the other hand, upon the surgeon turning the handle unit 165 of the first forceps 135 in the turning direction shown by arrow B1 in FIG. 22 from the normal state wherein the first forceps 135 and the handle unit 165 are kept straight as shown in FIG. 21, the jaw 163 of the manipulator-hand portion 156 is turned in the same turning direction as with the handle unit 165 corresponding to actions of the handle unit 165 so as to be positioned slanting upward away from the axial direction of the insertion portion 155 as shown by arrow B2 in FIG. 22. Note that the surgeon can operate the second forceps 136 in the same way as with the first forceps 135. The insertion portion 132 is supported by the support device 123, and accordingly, is kept stationary regardless of the aforementioned actions of the forceps 135 and 136.

Thus, the surgeon can operate the CCD camera serving as observing means and the forceps serving as surgical instruments independently of each other as described above.

Figure 27:
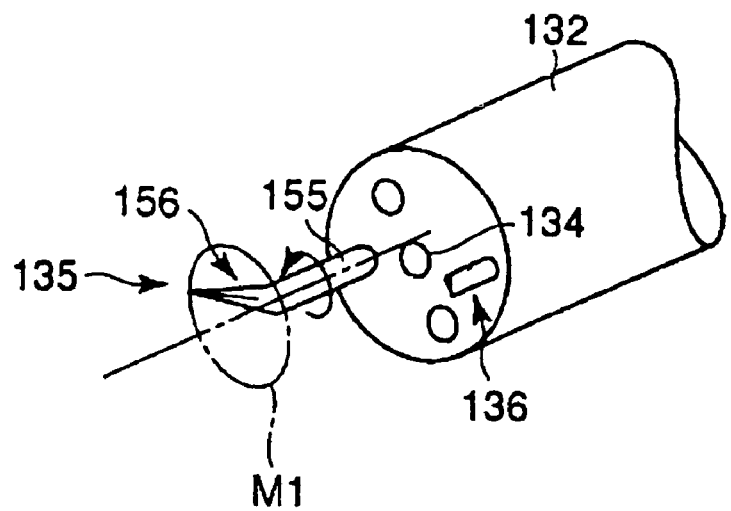

Furthermore, the surgical instrument 107 according to the present embodiment allows the surgeon to perform a wide range of operations using combinations of the aforementioned actions of the operation unit 122 and the actions of the first and second forceps 135 and 136. For example, FIG. 27 shows the action wherein the jaw 163 of the manipulator-hand portion 156 of the first forceps 135 is turned, and only the first forceps 135 is turned around the axis thereof while keeping the operation unit 122 stationary (not rotated). In this case, the tip of the jaw 163 of the manipulating-hand portion 156 of the first forceps 135 is turned in a relatively small turning range M1.

Figure 28:
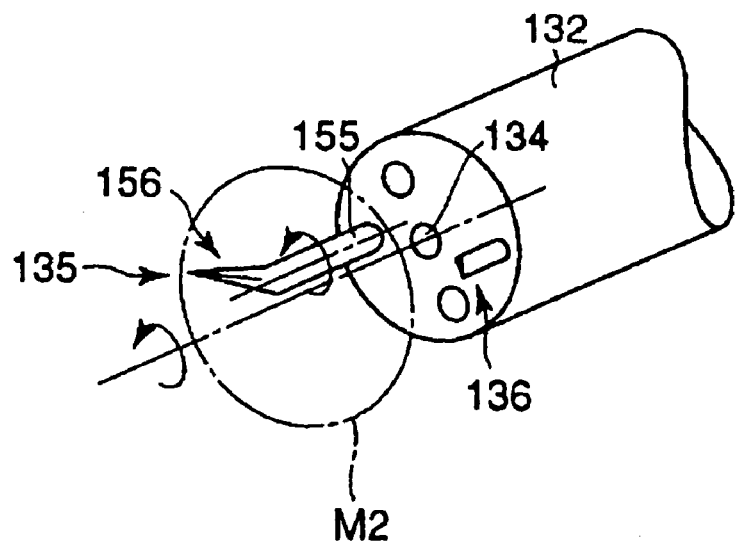

On the other hand, FIG. 28 shows the action wherein the jaw 163 of the manipulator-hand portion 156 of the first forceps 135 is turned in the same way as in FIG. 27, and the first forceps 135 is turned around the axis thereof while turning the entire operation unit 122 of the surgical instrument 107 in the same turning direction. In this case, the tip of the jaw 163 of the manipulating-hand portion 156 of the first forceps 135 is turned in a greater turning range M2 than the turning range M1 shown in FIG. 27.

Figure 29:
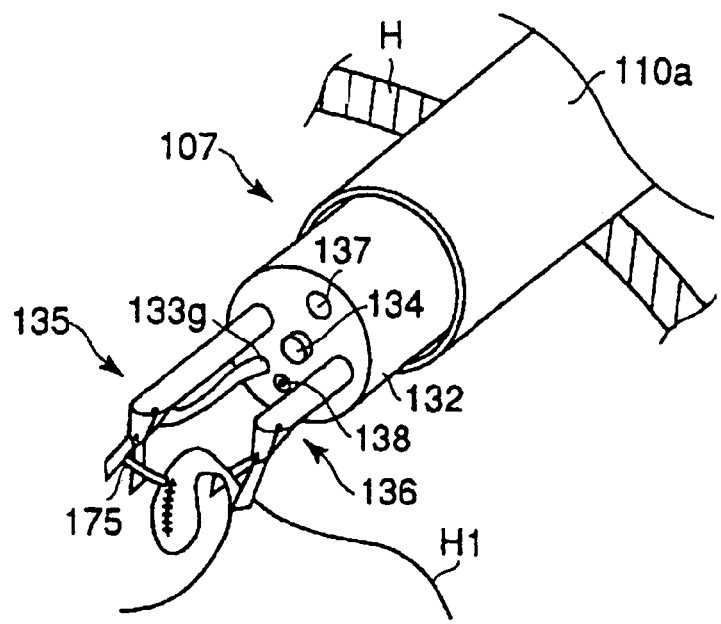
Figure 30:
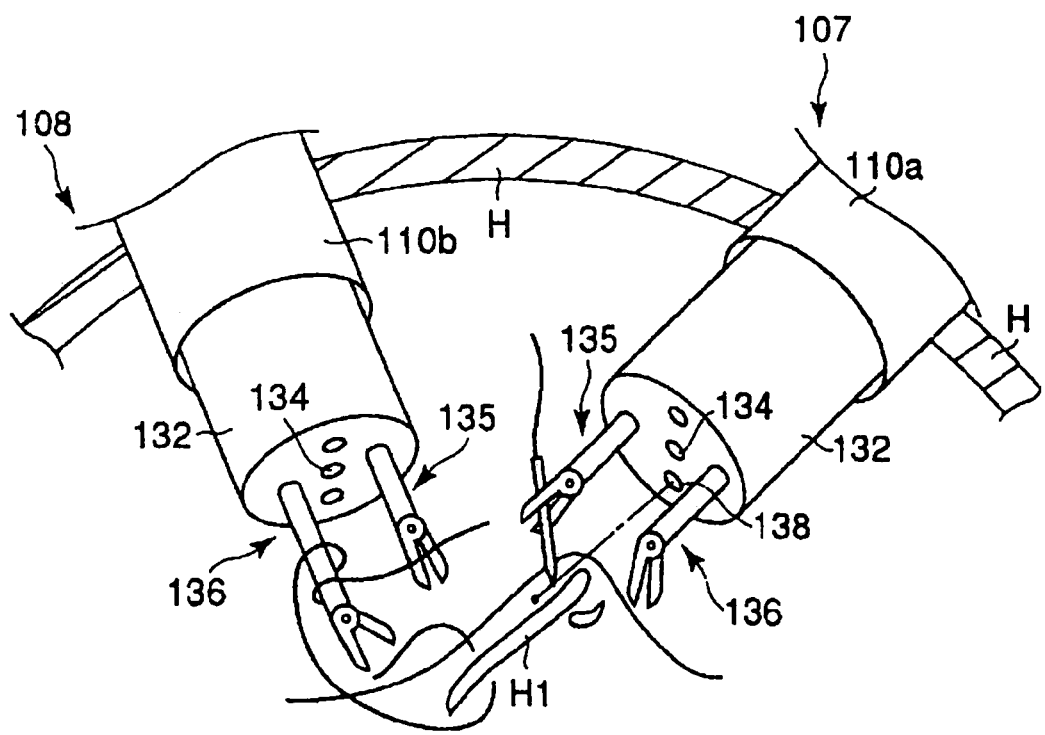

FIG. 29 is an explanatory diagram for describing an example of use of the surgical instrument 107 according to the present embodiment. In this case, the surgeon holds a part of tissue H1 which is to be subjected to medical treatment such as an organ in the body of the patient with the second forceps 136. Then, the surgeon inserts an surgical instrument such as an electrocauterizer 175 or the like through the channel 133g serving as a surgical-instrument through hole formed on the insertion portion 132. Subsequently, the surgeon holds the electrocauterizer 175 with the first forceps 135 so as to be guided to the tissue H1 which is to be subjected to medical treatment, following which the surgeon performs medical treatment for the tissue H1 with the electrocauterizer 175.

Thus, the surgical instrument having the aforementioned configuration has advantages as follows. That is to say, with the surgical instrument 107 according to the present embodiment, the manipulator-hand portion 156 serving as the tip of the first forceps 135 inserted into the channel 133b formed on the insertion portion 132 can be turned so as to be displaced from the axial direction of the insertion portion 155, thereby improving flexibility of operations of the first forceps 135, and thereby improving operability of the first forceps 135. Note that the second forceps 136 has the same advantages.

Furthermore, with the surgical instrument 107 according to the present embodiment, the insertion portion 132 of the single operation unit 122 includes the CCD camera 134 and the first and second forceps 135 and 136 therewithin, and thus, a single operator can perform operations for these components such as movement thereof at the same time. Furthermore, the positional relation between the CCD camera 134 and the first and second forceps 135 and 136 is maintained constant regardless of such movement of these components. This allows the operator to perform medical treatment in the body cavity with excellent operability, as if the operator were performing the medical treatment with his/her own hands while observing the medical treatment with his/her own eyes. Thus, surgery can be performed with a reduced number of openings formed on the body wall of the patient, as well as improving operability of the surgical instrument, thereby improving the ease of work involved in surgery.

Furthermore, the second forceps 136 is supported so as to be capable of sliding in the axial direction thereof in a range between the position where the tip-stopper pin 171 comes into contact with the tip face around the forceps guide opening formed on the insertion portion 132 and the position where the rear-end stopper pin 172 comes into contact with the rear-end face around the forceps guide opening formed on the insertion portion 132. Upon the surgeon pulling the second forceps 136 toward the surgeon such that the tip stopper pin 171 comes into contact with the tip face around the forceps guide opening formed on the insertion portion 132, and further pulling the second forceps 136 toward the surgeon, the entire operation unit 122 is moved toward the surgeon along the axial direction thereof while holding the forceps 136. On the other hand, upon the surgeon pressing the second forceps 136 in the direction away from the surgeon such that the rear-end stopper pin 172 comes into contact with the rear-end face around the forceps guide opening formed on the insertion portion 132, and further pressing the second forceps 136 in the direction away from the surgeon, the entire operation unit 122 is moved in the direction away from the surgeon along the axial direction thereof while holding the forceps 136.

Furthermore, in addition to movement of the operation unit 122 along the axial direction thereof by operating the second forceps 136 as described above, the surgeon can turn the entire operation unit 122 with the insertion point O of the trocar 110a formed on the body wall H of the patient as a center, in the first turning direction as shown by arrow A, and in the second direction shown by arrow B, independently of each other, i.e., in any turning direction, by operating the first and second forceps 135 and 136 as shown in FIG. 13. Thus, the operator can perform operations of the operation unit 122 while holding the first forceps 135 and the second forceps 136. This further improves workability of surgery.

Furthermore, the insertion portion 132 includes the two channels 133f and 133g serving as surgical-instrument through holes for inserting other surgical instruments, and the surgeon can perform medical treatment while holding the flexible surgical instruments inserted into the channels. Thus, the operator can perform medical treatment with various kinds of surgical instruments while holding the first and second forceps 135 and 136, i.e., without replacement of the surgical instruments, thereby reducing a period of time for surgery. Furthermore, the tip of each of the first and second forceps 135 and 136 can be turned with degree of freedom so as to be displaced from the axial direction thereof. This allows the surgeon to perform medical treatment with excellent operability in combination with use of the flexible surgical instruments.

With the endoscopic surgical system according to the present embodiment, surgery is performed using the surgical instruments having the aforementioned advantages, i.e., using the first surgical instrument 107 and the second surgical instrument 108 operated by the surgeon 103 and the second assistant 105, respectively. The endoscopic system according to the present embodiment further has advantages as follows.

The surgeon 103 and the second assistant 105 each operate his/her own surgical instruments 107 and 108, respectively, so as to perform surgery. Accordingly, the surgeon 103 and the second assistant 105 monitor images taken by his/her own surgical instruments in many situations. This leads to difficulty in that one operator (surgeon 103 or second assistant 105) follows the images monitored by another operator (second assistant 105 or surgeon 103). Furthermore, the images monitored by the surgeon 103 and the images monitored by the second assistant 105 are taken by different surgical instruments from different directions, leading to difficulty in that the surgeon 103 and the second assistant 105 follow the positional relation between these images. With the present embodiment, each of the first and second surgical instruments 107 and 108 cast a laser beam so as to form a laser beam spot on tissue in the body cavity. The laser beam spots thus formed on tissue are displayed as the indicating points 174a and 174b on the first monitor 111 and the second monitor 112 at the same time, and serve as common indicating points for the surgeon 103 and the second assistant 105.

Thus, the indicating points serve as means for assisting communication between the surgeon 103 and the second assistant 105. This mechanism allows the surgical staff members to perform surgery wherein the surgeon 103 sutures the tissue H1 with the first surgical instrument 107 and the second assistant 105 ties off a knot with the second surgical instrument 108 while communicating with each other, for example, thereby facilitating surgery. Furthermore, the first assistant 104 and the nurse 106 can monitor the indicating points 174a and 174b displayed on the first and second monitors 111 and 112, as well, thereby facilitating the first assistant 104 and the nurse 106 to assist surgery according to instructions from the surgeon 103 and the second assistant 105.

Thus, the endoscopic surgical system according to the present embodiment enables surgery with a reduced number of openings formed on the body wall of the patient, thereby reducing the load of the patient. Furthermore, the endoscopic surgical system enables surgery using various surgical instruments by a small number of surgical staff members. Furthermore, with the endoscopic surgical system according to the present embodiment, the first and second forceps 135 and 136 are formed with improved flexibility, thereby improving workability, and thereby enabling advanced and complicated surgery. In addition to these advantages, the endoscopic surgical system according to the present embodiment allows the surgical staff members to indicate a desired position on tissue in the body cavity in the form of a laser beam spot during endoscopic surgery. Thus, the surgical staff members can control the indicating points 174a and 174b serving as indicators displayed on the first and second monitors 111 and 112. This enables surgery to be performed by multiple surgical staff members such as a surgeon, assistants thereto, and so forth, in cooperation with each other while communicating each other. This leads to smooth surgery, resulting in reducing the load of the surgical staff members, as well as reducing a period of time for surgery. Furthermore, with the present embodiment, the first and second surgical instruments 107 and 108 may cast laser beams with different properties such as shape, color, or the like, so that the surgical staff members can discriminate between the two indicating points formed of the laser beam spots from these surgical instruments. This further facilitates communication between the surgical staff members, thereby enabling smooth surgery.

With the embodiments as described above, the surgery staff member can indicate a desired position on tissue in the body cavity with the indicating-point forming means during endoscopic surgery, thereby facilitating communication between the surgeon and the assistants. This enables surgery which is performed by multiple surgical staff members under endoscopic observation to be performed smoothly, thereby reducing the load of the surgical staff members, as well as reducing a period of time for surgery.

Note that the present invention is not restricted to the above embodiments, rather, it is needless to say that various modifications may be made without departing from spirit of the present invention.

What is claimed is:

1. A surgical system comprising:
a surgical instrument for medical treatment of an affected portion in a body cavity, the surgical instrument having an insertion portion for being inserted into the body cavity and an operating portion proximal to the insertion portion;
an observing device for observing the affected portion in the body cavity;
an image display device for displaying images taken by the observing device;
a control device for displaying an indicating-point to be superimposed on an image displayed on the image display device; and
an indicating-point control device which is included in the operating portion of the surgical instrument, for controlling the position of the indicating-point superimposed on the image displayed on the image display device.

2. A surgical system according to claim 1, wherein the observing device comprises an endoscope.

3. A surgical system according to claim 1, further comprising a switch which allows the surgeon to perform on/off control of an indicating-point forming device.

4. A surgical system according to claim 1, wherein the indicating-point control device comprises a joy-stick device.

5. A surgical system according to claim 4, further comprising a surgical instrument, wherein the joy-stick device is detachably mounted on the surgical instrument.

6. A surgical system according to claim 1, wherein the observing device has an operation unit therefore for moving the observing area thereof.

7. A surgical system according to claim 1, wherein the surgical instrument has an operation unit therefor.

8. A surgical system according to claim 1, further comprising an indicating-point forming device for casting an indicating point to the affected portion and forming an indicating point.

9. A surgical system according to claim 8, wherein the indicating-point control device controls the motion of the indicating point formed by the indicating-point forming device and cast to the affected portion.

10. A surgical system used in surgery performed by two or more surgical staff members, the surgical system comprising:
a surgical instrument for medical treatment of an affected portion in the body cavity, the surgical instrument having an insertion portion for being inserted into the body cavity and an operating portion proximal to the insertion portion;
an observation device for observing the affected portion in the body cavity;
an image display device for displaying images taken by the observation device to the two or more surgical staff members;
a control device for displaying an indicating-point to be superimposed on an image displayed on the image display device; and
an indicating-point control device included in the operating portion of the surgical instrument, for controlling the position of the indicating point superimposed on the image displayed on the image display device.

11. A surgical system used in surgery performed by two or more surgical staff members, the surgical system comprising:
a surgical instrument including two channels for inserting an observing device for observing an affected portion in the body cavity and forceps for medical treatment of the affected portion in the body cavity, the surgical instrument having an insertion portion for being inserted into the body cavity and an operating portion proximal to the insertion portion;
an image display device for displaying images taken by the observation device to the two or more surgical staff members respectively;
a control device for displaying an indicating-point to be superimposed on an image displayed on the image display device; and
an indicating-point control device included in the operating portion of the surgical instrument, for controlling the position of the indicating point superimposed on the image displayed on the image display device.

12. A surgical system used in surgery performed by two or more surgical staff members, the surgical system comprising:
a plurality of surgical instruments for medical treatment of an affected portion in the body cavity, at least one of the plurality of surgical instruments having an insertion portion for being inserted into the body cavity and an operating portion proximal to the insertion portion;
a plurality of sets of observing means for observing the affected portion in the body cavity;
a plurality of sets of image display means for displaying images taken by the plurality of sets of observing devices respectively;
a control device for displaying an indicating-point to be superimposed on an at least one of the images displayed on at least one of the plurality of sets of image display means; and
an indicating-point control device included in the operating portion of the at least one of the plurality of surgical instruments, for controlling the position of the indicating point superimposed on the at least one of the images displayed on the at least one of the plurality of sets of image display means.

13. A surgical system used in surgery performed by two or more surgical staff members, the surgical system comprising:
a plurality of surgical instruments each of which include two channels for inserting an observing device for observing an affected portion in the body cavity and forceps for medical treatment of the affected portion in the body cavity, at least one of the plurality of surgical instruments having an insertion portion for being inserted into the body cavity and an operating portion proximal to the insertion portion;
a plurality of sets of image display devices for displaying images taken by the corresponding observation devices included in the plurality of surgical instruments;

a control device for displaying an indicating-point to be superimposed on an at least one of the images displayed on at least one of the plurality of sets of image display devices; and an indicating-point control means included in the operating portion of the at least one of the plurality of surgical instruments, for controlling the position of the indicating point superimposed on the image displayed on the image display device.

14. A surgery method comprising:

a step for preparing a surgical instrument and an observation device for medical treatment of an affected portion in a body cavity, the surgical instrument having an insertion portion for being inserted into the body cavity and an operating portion proximal to the insertion portion;

a step for preparing an image display device for displaying images taken by the observation device;

a step for making openings on the body wall of the patient;

a step for inserting the surgical instrument and the observation device into the body cavity through the openings formed on the body wall of the patient;

a step for displaying an indicating-point to be superimposed on the image displayed on the image display device;

a step wherein the operator of the surgical instrument controls a position of the indicating point superimposed on the image displayed on the image display device from the operating portion of the surgical instrument; and a step wherein surgical staff members perform surgery while monitoring the indicating point.

15. A surgery method wherein two or more surgical staff members operate surgical instruments for medical treatment of an affected portion in the body cavity so as to perform surgery while monitoring images, which have been taken by an observation device for observing tissue in the body cavity, which are displayed on an image display device, comprising:

a step for making openings on the body wall of the patient;

a step for inserting the surgical instruments and the observation device into the body of the patient through the openings, at least one of the surgical instruments having an insertion portion for being inserted into the body cavity and an operating portion proximal to the insertion portion;

a step for displaying an indicating-point to be superimposed on the image displayed on the image display device;

a step wherein the operator of the surgical instrument controls the position of the indicating point superimposed on the image displayed on the image display device from the operating portion of the at least one surgical instrument; and a step wherein the two or more surgical staff members perform surgery while monitoring the indicating point.

16. A surgical system comprising:

a surgical instrument for medical treatment of an affected portion in the body cavity, the surgical instrument having an insertion portion for being inserted into the body cavity and an operating portion proximal to the insertion portion;

an observing device for observing the affected portion in the body cavity;

an image display device for displaying images taken by the observing device;

a control device for displaying an indicating-point to be superimposed on an image displayed on the image display device;

an indicating-point control device included in at least the operating portion of the surgical instrument, for controlling a position of the indicating point superimposed on the image displayed on the image display device, wherein the indicating-point control device comprises an indicating-point forming device for forming an indicating point serving as an indicator by casting light; and a switch for performing an on/off control of the indicating-point forming device.

* * * * *